United States Patent
Kajikawa et al.

(10) Patent No.: US 8,546,459 B2
(45) Date of Patent: Oct. 1, 2013

(54) DENTAL FILLING/RESTORATION KIT

(75) Inventors: Mihoko Kajikawa, Tokyo (JP); Takeshi Suzuki, Tokyo (JP)

(73) Assignee: Tokuyama Dental Corporation (JP)

( * ) Notice: Subject to any disclaimer, the term of this patent is extended or adjusted under 35 U.S.C. 154(b) by 0 days.

(21) Appl. No.: 13/147,030

(22) PCT Filed: Feb. 3, 2010

(86) PCT No.: PCT/JP2010/000650
§ 371 (c)(1),
(2), (4) Date: Jul. 29, 2011

(87) PCT Pub. No.: WO2010/090011
PCT Pub. Date: Aug. 12, 2010

(65) Prior Publication Data
US 2011/0288195 A1  Nov. 24, 2011

(30) Foreign Application Priority Data
Feb. 9, 2009  (JP) ................................. 2009-027018

(51) Int. Cl.
*C08L 33/12*  (2006.01)
(52) U.S. Cl.
USPC ................................. 522/11; 522/7; 522/33
(58) Field of Classification Search
USPC ............................................. 522/33, 11, 22
See application file for complete search history.

(56) References Cited

U.S. PATENT DOCUMENTS

| 5,530,038 A * | 6/1996 | Yamamoto et al. | 523/116 |
| 2003/0050359 A1 * | 3/2003 | Kimura et al. | 522/182 |
| 2004/0180983 A1 * | 9/2004 | Hara et al. | 522/33 |
| 2005/0009946 A1 * | 1/2005 | Oguri et al. | 522/184 |
| 2010/0216096 A1 | 8/2010 | Suzuki et al. | |

FOREIGN PATENT DOCUMENTS

| CN | 1537870 A | 10/2004 |
| DE | 602004001247 T2 | 5/2007 |
| EP | 1454921 A1 | 9/2004 |
| EP | 1457190 A1 | 9/2004 |
| JP | 63-273602 A | 11/1988 |
| JP | 2004-43427 A | 2/2004 |
| JP | 2005-89729 A | 4/2005 |
| JP | 2005-213231 A | 8/2005 |
| JP | 2006-56844 A | 3/2006 |
| JP | 2006-76912 A | 3/2006 |
| JP | 2009-13170 A | 1/2009 |
| JP | 2009-51826 A | 3/2009 |
| JP | 2009-215254 A | 9/2009 |
| JP | 2010-37324 A | 2/2010 |
| WO | 03/027153 A1 | 4/2003 |
| WO | 20081149929 A1 | 12/2008 |

OTHER PUBLICATIONS

International Search Report for International Application No. PCT/JP2010/000650 mailing date of Mar. 2, 2010 with English Translation.

\* cited by examiner

*Primary Examiner* — James J Seidleck
*Assistant Examiner* — Peter A Salamon
(74) *Attorney, Agent, or Firm* — Cantor Colburn LLP

(57) ABSTRACT

Provided is a filling/restoring material, including a photopolymerization initiator of a quaternary system formed by combining an α-diketone compound, an aliphatic amine compound, an aromatic amine compound, and a photoacid generator, in which even when the filling/restoring material is filled and cured on a cured layer of a dental adhesive material including a radical-polymerizable monomer having an acidic group, the filling/restoring material undergoes sufficient curing up to a contact interface between the filling/restoring material and the cured layer, thereby providing high adhesive strength stably. Also provided is a dental filling/restoration kit, including: a filling/restoring material including: a polymerizable monomer having no acidic group; a basic inorganic material; and a photopolymerization initiator formed by at least combining: an α-diketone compound; an aliphatic amine compound; an aromatic amine compound; and a photoacid generator; and an adhesive material, which is used for adhesion between a tooth and the filling/restoring material by curing the adhesive material before filling the filling/restoring material, the adhesive material including: a polymerizable monomer including a polymerizable monomer having an acidic group; and a polymerization initiator.

6 Claims, No Drawings

DENTAL FILLING/RESTORATION KIT

This is a U.S. national stage application of International Application No. PCT/JP2010/000650, filed on 3 Feb. 2010. Priority under 35 U.S.C. 119(a) and 35 U.S.C. 365(b) is claimed from Japanese Application No. JP 2009-027018, filed 9 Feb. 2009, the disclosure of which is also incorporated herein by reference.

BACKGROUND

1. Technical Field

The present invention relates to a dental filling/restoration kit, including a photopolymerizable filling/restoring material, and an adhesive material, which is used for adhesion between a tooth and the filling/restoring material by curing the adhesive material before filling the filling/restoring material.

2. Background Art

Conventionally, a small defect (cavity) formed because of the decay or the like of a tooth has been treated by filling a metal material. However, in recent years, a resin-based filling/restoring material containing a polymerizable monomer, an inorganic filler, and a polymerization initiator as its main components has been used preferentially instead of the metal material, because a color tone comparable to a natural tooth color can be imparted and its operation is easy. The resin-based filling/restoring material per se usually has no adhesive to a tooth, and hence the resin-based filling/restoring material and a tooth are generally caused to adhere to each other by interposing a dental adhesive material therebetween.

Further, the adhesive material also includes a polymerizable monomer and a polymerization initiator as its main components like the filling/restoring material, and the adhesiveness of the adhesive material to a tooth is enhanced by including a compound excellent in adhesiveness to a tooth as a part of the polymerizable monomer. A monomer containing an acidic group is particularly known to be suitable as such polymerizable monomer excellent in adhesiveness to a tooth. Further, such adhesive material including such polymerizable monomer having an acidic group as a polymerizable monomer is provided with a tooth demineralizing ability by additionally containing water, and the monomer having an acidic group is also excellent in permeability into a tooth. Thus, using the adhesive material is very advantageous, because it is possible to eliminate troublesome pretreatment usually performed for improving adhesiveness, that is, demineralization treatment with an acidic aqueous solution and permeation treatment with a polymerizable monomer excellent in affinity to a tooth.

By the way, in the resin-based filling/restoring material and its adhesive material described above, a photopolymerization initiator is advantageously used as the polymerization initiator because of its short curing time, its easy operability, and the like. In particular, there is preferably adopted a photopolymerization initiator whose functions are induced by visible light that is harmless to a living body. There are frequently used an α-diketone compound such as camphorquinone or a phosphorus-based compound such as an acylphosphine oxide as such visible light polymerization initiator. Of those, the α-diketone compound is very useful as a photopolymerization initiator for a filling/restoring material, because the use of the α-diketone compound in combination of an amine compound increases the curing rate of the filling/restoring material and makes the curing depth of the filling/restoring material larger.

Further, it is more preferred that the photocuring of the filling/restoring material can be performed by light irradiation in a shorter time, because a burden on a patient can be alleviated. It is proposed that, in order to perform the curing in a much shorter time, it is effective to use the α-diketone compound and the amine compound in combination of a photoacid generator such as an aryliodonium salt or a triazine compound (Patent Literatures 1 and 2). Further, it has been found that an aromatic amine compound is more active among amine compounds, and that, when not only the aromatic amine but also an aliphatic amine are used in combination in a system using the above-mentioned photoacid generator in combination, the curing activity of the aromatic amine compound is significantly improved, and the filling/restoring material is polymerized and cured in an extremely short time even in the case of using a weak light source (Patent Literature 3).

CITATION LIST

Patent Literature

Patent Literature 1: JP 63-273602 A
Patent Literature 2: JP 2005-89729 A
Patent Literature 3: JP 2005-213231 A

SUMMARY

As described above, a quaternary system formed by combining an α-diketone compound, an aliphatic amine compound, an aromatic amine compound, and a photoacid generator is very good as a photopolymerization initiator, because the quaternary system has a remarkably high curing activity and is capable of curing a filling/restoring material deeply. However, when the inventors of the present invention further advanced their studies by actually blending the photopolymerization initiator in a filling/restoring material, the inventors have found that, even when the filling/restoring material is cured on the cured surface of the adhesive material for a tooth containing a polymerizable monomer having an acidic group, sufficient adhesive strength is not provided with respect to a tooth by light irradiation for a short time. This is probably because a surface unpolymerized layer existing in the surface of the cured layer of the adhesive material, which serves as a substrate for curing the filling/restoring material, is significantly involved.

Specifically, the photopolymerization initiator includes an aliphatic amine compound and an aromatic amine compound as its components, but after the aliphatic amine compound forms a salt with an acid, the photopolymerization initiator almost loses the improving effect on the catalytic activity. Thus, when a curable composition including the photopolymerization initiator is filled on a substrate containing an acid content, the catalytic activity of the photopolymerization initiator decreases at its contact interface with the substrate, resulting in the suppression of a curing reaction. On the other hand, in the cured layer of the adhesive material, which serves as a substrate for curing the filling/restoring material, there exist acidic groups derived from components of polymerizable monomers having an acidic group. Note that each acidic group is firmly bound to a polymer, and hence its reactivity is weak. Thus, it is considered that, even when the filling/restoring material is filled and cured on the cured layer of the adhesive material, the neutralization of an amine compound contained in the photopolymerization initiator should not intrinsically give a significant influence on the reduction of the polymerization activity of the photopolymerization initiator at the contact interface between the filling/restoring material and the cured layer.

However, there exists a surface unpolymerized layer containing an unreacted radical-polymerizable monomer having an acidic group on the surface of the cured layer of an actual adhesive material. That is, an adhesive material applied to a tooth is cured in the state of being open to the air as a matter of course, and hence the polymerization reaction in the surface of the adhesive material is blocked by oxygen molecules in air, forming the above-mentioned surface unpolymerized layer. In the radical-polymerizable monomers each having an acidic group contained in the surface unpolymerized layer, the amount of calcium ions produced by demineralization is smaller compared with the radical-polymerizable monomers each having an acidic group, and hence their influence is small, the acidity level does not decrease, and the radical-polymerizable monomers each having an acidic group remain unreacted. The surface of the cured layer of the adhesive material is in the state of being highly reactive with an aliphatic amine compound. Thus, it is estimated that, even when the filling/restoring material including a photopolymerization initiator is filled on the surface of the cured layer and is cured, sufficient adhesive strength with respect to a tooth is not provided. That is, it is possible to be considered that, at their contact interface, an aliphatic amine compound included in the photopolymerization initiator in the filling/restoring material forms a salt with an acidic group in a radical-polymerizable monomer having an acidic group contained in the surface unpolymerized layer in the surface of the cured layer of the adhesive material, and hence the aliphatic amine compound does not contribute to improving the polymerization activity of the photopolymerization initiator, resulting in poor curing.

Note that the photopolymerization initiator also includes an aromatic amine compound, and hence it is estimated that the aromatic amine compound may form, at the above-mentioned contact interface, a salt with an acidic group in a radical-polymerizable monomer having an acidic group contained in the surface unpolymerized layer in the surface of the cured layer of the adhesive material. However, in general, an aliphatic amine compound is strongly basic, but an aromatic amine compound is weakly basic. Such weakly basic aromatic amine compound forms a salt with the above-mentioned acidic group reversibly and weakly, but the reactivity between an excited photopolymerization initiator and an amine compound is high in a photopolymerization reaction and an irreversible reaction takes place. Thus, the neutralization between the aromatic amine compound and the acidic group hardly affects the polymerization activity of the photopolymerization initiator.

In the above-mentioned background, the present invention has an object to eliminate the problems described above. Specifically, an object of the present invention is to provide a filling/restoring material, including a photopolymerization initiator of a quaternary system formed by combining an α-diketone compound, an aliphatic amine compound, an aromatic amine compound, and a photoacid generator, in which even when the filling/restoring material is filled and cured on a cured layer of a dental adhesive material including a radical-polymerizable monomer having an acidic group, the filling/restoring material undergoes sufficient curing up to a contact interface between the filling/restoring material and the cured layer, thereby providing high adhesive strength stably.

The inventors of the present invention have intensively continued their studies in order to accomplish the above-mentioned object. As a result, the inventors have found that the problems are solved by additionally including a basic inorganic material in the filling/restoring material formed by combining an α-diketone compound, an aliphatic amine compound, an aromatic amine compound, and a photoacid generator, the filling/restoring material being filled on the cured layer of a dental adhesive material containing a polymerizable monomer having an acidic group. As a result, the present invention has been completed.

That is, a dental filling/restoration kit of the present invention includes: a filling/restoring material (A) including: a polymerizable monomer having no acidic group (I); a basic inorganic material (II); and a photopolymerization initiator (III) formed by at least combining: an α-diketone compound (i); an aliphatic amine compound (ii); an aromatic amine compound (iii); and a photoacid generator (iv); and an adhesive material (B), which is used for adhesion between a tooth and the filling/restoring material by curing the adhesive material before filling the filling/restoring material, the adhesive material including: a polymerizable monomer including a polymerizable monomer having an acidic group (I); and a polymerization initiator (II).

Further, according to one embodiment of the dental filling/restoration kit of the present invention, it is preferred that the filling/restoring material (A) include the basic inorganic material (II) in an amount of at least 3 parts by mass with respect to 100 parts by mass of the polymerizable monomer having no acidic group (I).

In addition, according to another embodiment of the dental filling/restoration kit of the present invention, it is preferred that the filling/restoring material (A) include tertiary amine compounds as the aliphatic amine compound (III) (ii) and the aromatic amine compound (III) (iii).

In addition, according to another embodiment of the dental filling/restoration kit of the present invention, it is preferred that the filling/restoring material (A) include fluoroaluminosilicate glass as the basic inorganic material (II).

In addition, according to another embodiment of the dental filling/restoration kit of the present invention, it is preferred that the adhesive material (B) further include water (III).

In addition, according to another embodiment of the dental filling/restoration kit of the present invention, it is preferred that the adhesive material (B) include a polymerizable monomer having a phosphate acidic group as an acidic group as the polymerizable monomer including a polymerizable monomer having an acidic group (I).

In addition, according to another embodiment of the dental filling/restoration kit of the present invention, it is preferred that the filling/restoring material (A) include a filler (IV).

In addition, according to another embodiment of the dental filling/restoration kit of the present invention, it is preferred that the dental filling/restoration kit consist of the filling/restoring material (A) and the adhesive material (B).

The filling/restoration kit of the present invention includes the filling/restoring material containing a basic inorganic material. Hence, even when the polymerizable monomer having an acidic group exists in the surface unpolymerized layer, the basic inorganic material neutralizes the acidic group of the polymerizable monomer competitively or preferentially at the contact interface of the filling/restoring material filled on the cured layer of the adhesive material. As a result, the neutralization of the aliphatic amine compound in the photopolymerization initiator contained in the filling/restoring material is significantly reduced, and hence the filling/restoring material undergoes sufficient curing up to the contact interface with the cured layer of the adhesive material owing to the high polymerization activity. Thus, there is provided a dental filling/restoration kit that is capable of realizing stably high adhesive strength between a tooth and the filling/restoring material even when light irradiation is performed in an extremely short time.

Further, the filling/restoration kit of the present invention includes the filling/restoring material (A) containing the basic inorganic material (II) in an amount of at least 3 parts by mass with respect to 100 parts by mass of the polymerizable monomer having no acidic group (I), and hence the basic inorganic material can sufficiently perform an neutralization action with an acid content contained in the surface unpolymerized layer of the adhesive material, resulting in being able to further enhance the adhesiveness between the filling/restoring material and a tooth.

In addition, the filling/restoration kit of the present invention includes the filling/restoring material (A) containing tertiary amine compounds as the aliphatic amine compound (III) (ii) and the aromatic amine compound (III) (iii), and hence the polymerization activity of the photopolymerization initiator contained in the filling/restoring material can be particularly enhanced.

In addition, the filling/restoration kit of the present invention includes the filling/restoring material (A) containing fluoroaluminosilicate glass as the basic inorganic material (II), and hence the neutralization of acidic groups existing in the cured layer of the adhesive material is performed by polyvalent metal ions eluted from the fluoroaluminosilicate glass. As a result, ion bridges are formed between the neutralized acidic groups via the polyvalent metal ions, resulting in further improvement in the strength of the contact interface between the cured layer of the adhesive material and the filling/restoring material.

In addition, the filling/restoration kit of the present invention includes (B) the adhesive material further containing water (III), and hence it is possible to impart the adhesive material with a tooth demineralizing function and a permeation function into a tooth of a polymerizable monomer with an affinity. As a result, the adhesive material can realize the effect of highly adhering to a tooth in a form excellent in operability attained by eliminating the above-mentioned pretreatment.

DETAILED DESCRIPTION

A dental filling/restoration kit according to this embodiment includes, broadly speaking, a filling/restoring material and an adhesive material as its components.

[Filling/Restoring Material (A)]

The filling/restoring material includes a polymerizable monomer having no acidic group (I), a basic inorganic material (II), a photopolymerization initiator (III) formed by at least combining an α-diketone compound (i), an aliphatic amine compound (ii), an aromatic amine compound (iii), and a photoacid generator (iv), and a filler (IV). Hereinafter, the details of each component included in the filling/restoring material are described.

(A) Polymerizable Monomer Having No Acidic Group (I)

In the dental filling/restoration kit according to this embodiment, any polymerizable monomer having no acidic group in its molecule can be used without any limitation, as a polymerizable monomer having no acidic group to be included in the filling/restoring material. Here, the term "acidic group" refers to a functional group which has a pKa of less than 5 and from which an active proton can be dissociated, such as a phosphinico group, a phosphono group, a sulfo group, or a carboxyl group.

As such polymerizable monomer having no acidic group, a (meth)acrylate-based monomer is used mainly due to the satisfactory polymerization property or the like. Specific examples of the (meth)acrylate-based monomer include ones described in the following items (1) to (4).

(1) Monofunctional Polymerizable Monomer

Examples of the monofunctional polymerizable monomer include: alkyl esters of (meth)acrylates such as ethylhexyl (meth)acrylate, isodecyl(meth)acrylate, n-lauryl(meth)acrylate, tridecyl (meth)acrylate, n-stearyl(meth)acrylate, cyclohexyl (meth)acrylate, benzyl(meth)acrylate, phenoxyethyl (meth)acrylate, isobornyl(meth)acrylate, 2-hydroxyethyl (meth)acrylate, 3-hydroxypropyl(meth)acrylate, tetrahydrofurfuryl(meth)acrylate, and glycidyl(meth)acrylate; fluorine-containing (meth)acrylates such as 1H, 1H, 3H-hexafluorobutyl methacrylate, 1H, 1H, 5H-octafluoropentyl methacrylate, 1H, 1H, 6H-decafluorohexyl methacrylate, and 1H, 1H, 7H-dodecafluoroheptyl methacrylate; and (meth)acrylates represented by the following formulaes.

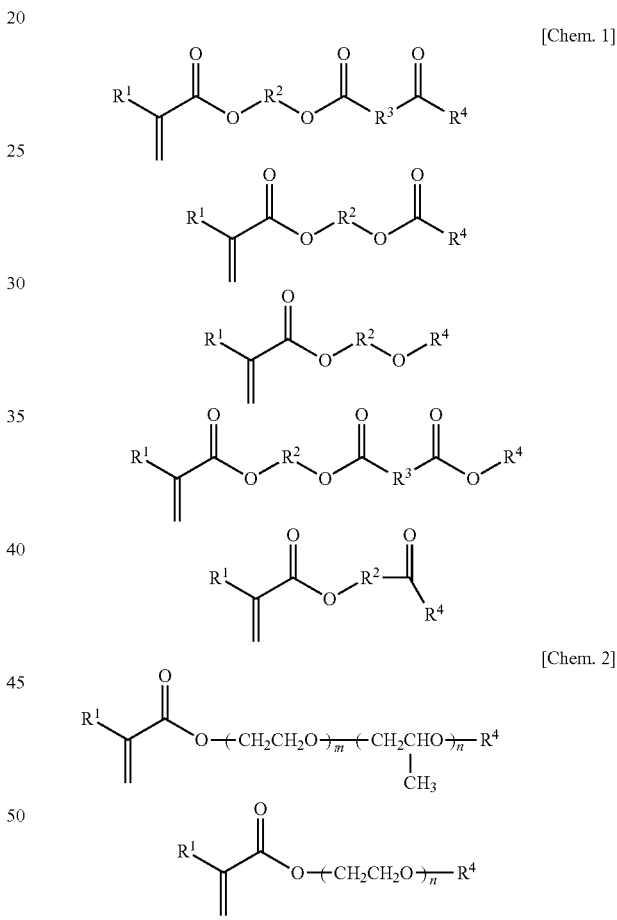

It should be noted that $R^1$ in each of the above-mentioned formulae represents a hydrogen atom or a methyl group. Further, $R^2$ and $R^3$ in each of the above-mentioned formulae each independently represent an alkylene group. Further, $R^4$ in each of the above-mentioned formulae represents an alkyl group. In each of the above-mentioned formulae, m represents 0 or an integer of 1 to 10 and n represents an integer of 1 to 10 (provided that m+n represents an integer of 2 to 10).

(2) Bifunctional Polymerizable Monomer

Examples of the bifunctional polymerizable monomer include ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, 1,3-butanediol di(meth), 1,4-butanediol di(meth)acrylate, 1,6-hexanediol di(meth)acrylate, 1,9-nonanediol di(meth)acrylate, 1,10-decanediol di(meth)acrylate, 2,2-bis((meth)acryloxyphenyl) propane, 2,2-bis[4-(3-(meth)acryloxy)-2-hydroxypropoxyphenyl]propane, 2,2-bis(4-(meth)acryloxyethoxyphenyl)propane, 2,2-bis(4-(meth)acryloxydiethoxyphenyl)propane, 2,2-bis(4-(meth)acryloxytetraethoxyphenyl)propane, 2,2-bis(4-(meth)acryloxypentaethoxyphenyl)propane, 2,2-bis(4-(meth)acryloxydipropoxyphenyl)propane, 2-(4-methacryloxyethoxyphenyl)-2-(4-(meth)acryloxydiethoxyphen yl)propane, 2-(4-(meth)acryloxydiethoxyphenyl)-2-(4-(meth)acryloxytriethox yphenyl)propane, 2-(4-(meth)acryloxydipropoxyphenyl-2-(4-(meth)acryloxytriethox yphenyl)propane, 2,2-bis(4-(meth)acryloxypropoxyphenyl)propane, and 2,2-bis(4-(meth)acryloxyisopropoxyphenyl)propane.

(3) Trifunctional Polymerizable Monomer

Examples of the trifunctional polymerizable monomer include trimethylolpropane tri(meth)acrylate, trimethylolethane tri(meth)acrylate, pentaerythritol tri(meth)acrylate, and trimethylolmethane tri(meth)acrylate.

(4) Tetrafunctional Polymerizable Monomer

Examples of the tetra functional polymerizable monomer include pentaerythritol tetra(meth)acrylate, ditrimethylolpropane tetra(meth)acrylate, and pentaerythritol hexa(meth)acrylate.

Further, of the above-mentioned polymerizable monomers having no acidic group, radical-polymerizable monomers having two or more functional groups are preferred in terms of the mechanical strength.

In the dental filling/restoration kit according to this embodiment, the polymerizable monomer as described above may be used alone or two or more kinds thereof may be used together. Further, a plurality of kinds of polymerizable monomers having different numbers of functional groups may be combined.

(A) Basic Inorganic Material (II)

In the dental filling/restoration kit according to this embodiment, the basic inorganic material included in the filling/restoring material improves the strength of the filling/restoring material by a filler effect and exerts the effect of highly retaining the polymerization activity of the photopolymerization initiator described below at the contact interface of the filling/restoring material with the cured layer of the adhesive material at the time of polymerization. Specifically, it is estimated that the basic inorganic material neutralizes the acid content contained in the surface unpolymerized layer in the cured layer of the adhesive material competitively with or preferentially than an aliphatic amine compound (II), which is a component of the photopolymerization initiator, thereby preventing the aliphatic amine compound from being deactivated.

Any known basic inorganic material can be used as the basic inorganic material described above without any limitation. However, from the viewpoint of suppressing more efficiently neutralization of one of components, i.e., the aliphatic amine compound (III) (ii), a basic inorganic material having a high degree of basicity is preferred, because it is preferred that the basic inorganic material react with an acidic group in the radical-polymerizable monomer having an acidic group as preferentially as possible than the aliphatic amine compound. In this sense, usually used is a basic inorganic material showing a high degree of basicity measured by the following method. That is, to 20 g of an acidic solution obtained by dropping phosphoric acid to a solution prepared by mixing distilled water and ethanol in a volume ratio of 1:1 in a beaker having a base area of 706.5 mm$^2$ in its inner space portion, and adjusting the pH of the resultant solution to 2.50±0.03 at 23° C., 1.0 g of a basic inorganic material is added, the whole is stirred at 23° C. for 2 minutes at a rotation number of 200 rpm by using a stirrer with a diameter of 8 mm and a length of 20 mm, and the pH of the solution is measured immediately. When the solution exhibits a pH differential value higher by preferably 0.05 or more, more preferably 0.1 or more, compared with the solution free of the basic inorganic material, the basic inorganic material is used. Note that when the degree of basicity of a basic inorganic material is too high, the storage stability of an a filling/restoring material may lower, and hence the upper limit of the pH differential value is preferably 4.5, particularly preferably 2.0. In order to carry out the above-mentioned method of measuring pH, it is recommended that a glass electrode using a potassium chloride solution be used and a pH meter be immersed in a solution under stirring, thereby performing measurement.

Note that the basic inorganic material included in the filling/restoring material also functions as a filler. Thus, the filling/restoring material according to this embodiment is "a filling/restoring material including (A) a polymerizable monomer having no acidic group (I), a basic inorganic material (II), a photopolymerization initiator (III) formed by at least combining an α-diketone compound (i), an aliphatic amine compound (ii), an aromatic amine compound (iii), and a photoacid generator (iv), and a filler (IV)." Specifically, the filling/restoring material according to this embodiment is broadly classified into the following two kinds.

<First Filling/Restoring Material>

The first filling/restoring material includes a polymerizable monomer having no acidic group (I), a basic inorganic material (II, IV) (having a function of a filler for the basic inorganic material), and a photopolymerization initiator (III) formed by at least combining an α-diketone compound (i), an aliphatic amine compound (ii), an aromatic amine compound (iii), and A photoacid generator (iv).

<Second Filling/Restoring Material>

The second filling/restoring material includes a polymerizable monomer having no acidic group (I), a basic inorganic material (II), a photopolymerization initiator (III) formed by at least combining an α-diketone compound (i), an aliphatic amine compound (ii), an aromatic amine compound (iii), and a photoacid generator (iv), and a filler (IV) (which is a filler excluding the basic inorganic material).

Note that in the second filling/restoring material, the ratio of the basic inorganic material in the mixed filler component of the basic inorganic material and the filler is preferably 0.03% by mass or more and 70% by mass or less, more preferably 1.0% by mass or more and 50% by mass or less. When the ratio of the basic inorganic material in the mixed filler component is controlled to 0.5% by mass or more, it is possible to secure reliably the effect of promoting polymerization induced by the aliphatic amine compound at the time of the polymerization of the filling/restoring material up to at its contact interface with the cured layer of the adhesive material.

An inorganic compound that can be used as the basic inorganic material is not limited as long as the inorganic compound satisfies the above-mentioned conditions, and can be preferably selected from oxides, hydroxides, fluorides, carbonates, and silicates of elements belonging to the Groups I, II, and III, mixtures thereof, combined salts thereof, and the like. Typical specific examples of the basic inorganic material include oxides such as alumina, calcia, and magnesia. Further examples thereof include hydroxides such as calcium hydroxide, magnesium hydroxide, and strontium hydroxide, fluorides such as sodium fluoride and calcium fluoride, and carbonates such as calcium carbonate, magnesium carbonate, and strontium carbonate. Further examples thereof include silicates such as caclium silicate, aluminum silicate, fluoroaluminosilicate glass, and other silicate glass. Of those, basic inorganic materials eluting metal ions such as a calcium ion and an aluminum ion may be suitably used.

From the viewpoint of adhesive strength, basic inorganic materials eluting bivalent or more polyvalent metal ions are more preferred and basic inorganic materials eluting trivalent or more polyvalent metal ions are particularly preferred. Of the basic inorganic materials eluting trivalent or more polyvalent metal ions, fluoroaluminosilicate glass is used most preferably. When the filling/restoring material is applied on the cured layer of the adhesive material, metal ions are eluted from the basic inorganic material eluting metal ions such as the fluoroaluminosilicate glass by an action of a polymerizable monomer having an acidic group existing in the surface unpolymerized layer and an action of water (moisture in an oral cavity or water that remains after drying treatment such as air blowing in the case when an adhesive material contains water), and hence the basic inorganic material eluting metal ions exerts the effect of reducing neutralization of an aliphatic amine compound. Further, aluminum ions and other polyvalent metal ions that are added in the composition as required eluted from fluoroaluminosilicate glass are particularly preferred, because ion bridges are formed between polymer substances of polymerizable monomers each having an acidic group at the contact interface with the cured layer of the adhesive material, thereby being able to further improve the adhesiveness with a tooth.

Any known fluoroaluminosilicate glass used for a cement for dental use such as a glass ionomer cement may be suitably used for the above-mentioned fluoroaluminosilicate glass. The composition of generally known fluoroaluminosilicate glass, which is suitably used, is, in terms of ion mass percent, 10 to 33 of silicon; 4 to 30 of aluminum; 5 to 36 of alkali earth metals; 0 to 10 of alkali metals; 0.2 to 16 of phosphorus; 2 to 40 of fluorine; and oxygen, the balance. A more preferred composition range is, for example, 15 to 25 of silicon; 7 to 20 of aluminum; 8 to 28 of alkali earth metals; 0 to 10 of alkali metals; 0.5 to 8 of phosphorus; 4 to 40 of fluorine; and oxygen, the balance. A compound in which a part or all of the calcium is substituted with magnesium, strontium, or barium is preferred. Further, although sodium is the most typical of the alkali metals, a compound in which a part or all of the sodium is substituted with lithium or potassium is also suitable. Further, as required, a part of the aluminum may be substituted with yttrium, zirconium, hafnium, tantalum, lanthanum, or the like.

After 0.1 g of each kind of fluoroaluminosilicate glass is immersed and retained in 10 ml of a 10 wt % maleic acid aqueous solution at a temperature of 23° C. for 24 hours, the amount of polyvalent metal ions eluted from the fluoroaluminosilicate glass is measured by an inductively coupled plasma (ICP) emission spectral analysis, an atomic absorption analysis, or the like, yielding a "24-hour elution ion amount." The "24-hour elution ion amount" is preferably 5.0 to 500 meq/g of glass, more preferably 10 to 100 meq/g of glass, particularly preferably 15 to 50 meq/g of glass. Fluoroaluminosilicate glass having any of the "24-hour elution ion amounts" described above exhibits a satisfactory degree of basicity, and a filling/restoring material can be easily produced by using this glass.

There is no particular limit to the shape of the basic inorganic material that can be used in the dental filling/restoration repair kit of the present invention. Crushed particles obtained by ordinary crushing or spherical particles may be used, and if required, particles in a plate shape, a fiber shape, or the like can also be mixed. Further, the basic inorganic material has an average particle size in the range of preferably 0.01 μm to 20 μm, more preferably 0.05 μm to 15 μm, still more preferably 0.1 μm to 5 μm, from the viewpoint that the neutralization reaction with the above-mentioned monomer having an acidic group is accelerated and the operability is not degraded. Further, from the viewpoint of rapidly promoting the neutralization reaction, the basic inorganic material has a specific surface area preferably in the range of 5 to 100 m$^2$/g (a value obtained by measuring the adsorption amount of nitrogen of the surfaces of particles by using a BET method), more preferably in the range of 10 to 60 m$^2$/g.

When the above-mentioned basic inorganic material is treated with a surface treatment agent typified by a silane coupling agent, it is possible to improve its affinity to a monomer, its dispersibility into a monomer, and the mechanical strength and water resistance of a cured body. Such surface treatment agent and surface treatment method are not particularly limited, and any known method can be adopted. Preferred examples of the silane coupling agent that is used for the surface treatment of the basic inorganic material include methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy)silane, γ-methacryloyloxypropyltrimethoxysilane, γ-chloropropyltrimethoxysilane, γ-glycidoxypropyltrimethoxysilane, and hexamethyldisilazane. Further, in addition to the silane coupling agent, the surface treatment of the basic inorganic material can be performed by a method using a titanate-based coupling agent, an aluminate-based coupling agent, or a zirco-aluminate-based coupling agent, or a method in which the monomer is graft polymerized onto the surface of a filler particle.

The blending ratio of the basic inorganic material in the filling/restoring material is not particularly limited, and is usually 3 parts by mass or more with respect to 100 parts by mass of the polymerizable monomer having no acidic group. The blending ratio of the basic inorganic material is preferably in this range, because the reactivity of the basic inorganic material with a polymerizable monomer having an acidic group is enhanced at the contact interface with the cured layer of the adhesive material. The blending ratio of the basic inorganic material is particularly preferably 5 to 80 parts by mass with respect to 100 parts by mass of the polymerizable monomer having no acidic group, most preferably 10 to 30 parts by mass.

(A) Photopolymerization Initiator (III)

The filling/restoring material forming the dental filling/restoration kit according to this embodiment includes a photopolymerization initiator formed by combining an α-diketone compound (i), an aliphatic amine compound (ii), an aromatic amine compound (iii), and a photoacid generator (iv). α-Diketone compound (i)

Examples of the α-diketone compound include α-diketone compounds such as diacetyl, 2,3-pentadione, 2,3-hexadione, benzil, 4,4'-dimethoxybenzil, 4,4'-diethoxybenzil, 4,4'-oxybenzil, 4,4'-dichlorbenzil, 4-nitrobenzil, α-naphthil, β-naphthil, camphorquinone, camphorquinone sulfonate, camphorquinone carboxylate, and 1,2-cyclohexanedione.

Those α-diketone compounds are preferred in terms of stability, and of those α-diketone compounds, diacetyl, benzil, and camphorquinone are particularly preferred.

The blending ratio of the α-diketone compound in the filling/restoring material is not particularly limited, and is usually controlled preferably in the range of 0.01 to 5 parts by mass, more preferably in the range of 0.1 to 3 parts by mass with respect to 100 parts by mass of the polymerizable monomer having no acidic group, from the viewpoint of keeping the level of the polymerization activity of the photopolymerization initiator high.

Aliphatic Amine Compound (ii)

In the dental filling/restoration kit according to this embodiment, the aliphatic amine compound is a compound in which all organic groups bonded to a nitrogen atom are aliphatic groups (which may have substituents). It is suitable to use as the compound a highly basic aliphatic amine compound in which the corresponding ammonium salt has a pKa of 7 or more, preferably 7.5 or more in water at 25° C.

Specific examples of the aliphatic group bonded to the nitrogen atom of the aliphatic amine compound include: linear or branched alkyl groups having 1 to 6 carbon atoms, such as a methyl group, an ethyl group, a propyl group, an n-butyl group, and an i-butyl group; and alkenyl groups such as an ethenyl group (vinyl group) and an allyl group. Further, examples of the substituent bonded to the aliphatic group include: aryl groups such as a phenyl group; a hydroxy group (substituted aliphatic group is, for example, a 2-hydroxyethyl group, a 2-hydroxypropyl group, a 2-hydroxybutyl group, or a 2,3-dihydroxypropyl group); halogen atoms such as a fluorine atom, a chlorine atom, and a bromine atom; acyloxy groups having 1 to 3 carbon atoms, such as an acetyloxy group, an acryloyloxy group, and a methacryloyloxy group; alkoxyl groups having 1 to 3 carbon atoms, such as a methoxy group, an ethoxy group, and a propoxy group; a carbonyl group; carbonyloxy group; and a cyano group.

Specific examples of such aliphatic amine compound include: aliphatic primary amine compounds such as 2-ethylhexylamine, n-butylamine, n-hexylamine, and n-octylamine; and aliphatic secondary amine compounds such as diethylamine, dibutylamine, diallylamine, diisopropylamine, di-2-ethylhexylamine, and di-n-octylamine. However, an aliphatic tertiary amine compound is preferred because of its high catalytic activity. Specific examples of the aliphatic tertiary amine compound include aliphatic tertiary amine compounds such as triethylamine, tributylamine, triallylamine, N,N-dimethylaminoethyl methacrylate, N,N-diethylaminoethyl methacrylate, N-methyldiethanolamine, N-ethyldiethanolamine, N-propyldiethanolamine, N-ethyldiallylamine, N-ethyldibenzylamine, dimethylethanolamine, diethylethanolamine, dipropylethanolamine, triethanolamine, tri(isopropanol)amine, tri(2-hydroxybutyl)amine, and tribenzylamine. A mixture of two or more kinds of those aliphatic tertiary amine compounds may also be used.

Of the above-mentioned aliphatic tertiary amine compounds, from the viewpoint of, for example, chemical stability of the compound, and excellent solubility in the monomer, it is preferred to use N,N-dimethylaminoethyl methacrylate, N,N-diethylaminoethyl methacrylate, N-methyldiethanolamine, N-ethyldiethanolamine, N-propyldiethanolamine, N-ethyldiallylamine, N-ethyldibenzylamine, dimethylethanolamine, diethylethanolamine, triethylamine, triethanolamine, and tributylamine are preferably used. In particular, N,N-dimethylaminoethyl methacrylate, dimethylethanolamine, and triethanolamine are most preferably used.

The blending ratio of the aliphatic amine compound in the filling/restoring material is preferably in the range of 0.0005 to 25 parts by mass with respect to 100 parts by mass of the polymerizable monomer having no acidic group, because a too small blending ratio may lead to an insufficient effect of improving the polymerization activity of the photopolymerization initiator. Further, because the aliphatic amine compound has a high basicity, blending the aliphatic amine compound at a large ratio is liable to cause a change in color in a cured body, and hence its blending ratio is controlled preferably as low as possible, from the viewpoint of highly suppressing the change, thereby forming a filling/restoring material excellent in aesthetics. In view of the foregoing, the blending ratio of the aliphatic amine compound is particularly preferably 0.05 to 5 parts by mass, more preferably 0.1 to 3 parts by mass with respect to 100 parts by mass of the polymerizable monomer having no acidic group. In the dental filling/restoration kit according to this embodiment, the blending ratio of the aliphatic amine compound is smaller as described above, but a sufficient polymerization activity can be exerted even at the contact interface with the cured layer of the adhesive material owing to the above-mentioned effect of blending the basic inorganic material (II), and hence it is possible to achieve both of a high adhesive force and a satisfactory color tone of the cured layer of the adhesive material.

Aromatic Amine Compound (iii)

In the dental filling/restoration kit according to this embodiment, any known aromatic amine compound can be used without any limitation, as long as the aromatic amine compound is an amine compound in which at least one of the organic groups bonded to the nitrogen atom is an aromatic group. It is suitable to use as the compound an aromatic amine compound in which the corresponding ammonium salt has a pKa of 6 or less in water at 25° C.

Specific examples of such aromatic amine compound include an aromatic primary amine compound such as aniline or toluidine and an aromatic secondary amine compound such as N-methylaniline or N-methyl-p-toluidine, but an aromatic tertiary amine compound is preferred from the viewpoint of its high polymerization activity.

A typical aromatic tertiary amine compound is an amine compound in which at least one or more aromatic groups and at most two or less aliphatic groups are bonded to the nitrogen atom of an amino group. There is exemplified particularly preferably an aromatic tertiary amine compound represented by the following general formula from the standpoint of having a higher polymerization activity.

[Chem. 3]

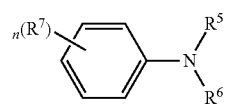

In the formula, $R^5$ and $R^6$ each independently represent an alkyl group, $R^7$ represents an alkyl group, an aryl group, an alkenyl group, an alkoxy group, a cyano group, a carbonyl group, an aminocarbonyl group, an alkyloxycarbonyl group, or the like. Further, n represents an integer of 0 to 5. In the case where n represents 2 or more, a plurality of $R^7$'s may or may not be the same. Further, $R^7$'s may be combined with each other to form a ring.

The alkyl group in each of $R^5$, $R^6$, and $R^7$ preferably represents a linear or branched alkyl group having 1 to 6 carbon atoms, and examples thereof include a methyl group, an ethyl group, an n-propyl group, an i-propyl group, an n-butyl group, and an n-hexyl group. Further, the alkyl group may be a substituted alkyl group having a substituent, and examples of such substituted alkyl group include a halogen-substituted alkyl group such as a fluoromethyl group and 2-fluoroethyl group, and a hydroxyl group-substituted alkyl group such as a 2-hydroxyethyl group.

Further, any of the aryl group, alkenyl group, alkoxy group, cyano group, carbonyl group, aminocarbonyl group, alkyloxycarbonyl group, and the like in $R^7$ may have a substituent. Examples of the aryl group include a phenyl group, a p-methoxyphenyl group, a p-methylthiophenyl group, a p-chlorophenyl group, and a 4-biphenyl group each having 6 to 12 carbon atoms. Examples of the alkenyl group include a vinyl group, a propenyl group, and a 2-phenylethenyl group each having 2 to 12 carbon atoms. Examples of the alkoxy group include a methoxy group, an ethoxy group, and a butoxy group each having 1 to 10 carbon atoms, examples of the carbonyl group include a formyl group, an acetyl group, a propionyl group, and a benzoyl group, examples of the aminocarbonyl group include an aminocarbonyl group, a methylaminocarbonyl group, and a dimethylaminocarbonyl group, and examples of the alkyloxycarbonyl group include a methoxycarbonyl group, an ethoxycarbonyl group, a butoxycarbonyl group, an aminoxycarbonyl group, and an isoamyloxycarbonyl group in each of which an alkyloxy group has 1 to 10 carbon atoms.

In the aromatic tertiary amine compound represented by the above-mentioned general formula, an alkyl group having 1 to 6 carbon atoms is preferred as each of $R^5$ and $R^6$. In particular, a unsubstituted alkyl group (e.g., a methyl group, an ethyl group, an n-propyl group) having 1 to 3 carbon atoms or a 2-hydroxyethyl group is more preferred. Of those, a methyl group is more preferred.

Further, in the case where n=1, the bonding position of $R^7$ is preferably a para-position. In particular, $R^7$ preferably represents an alkyl group or an alkyloxycarbonyl group, and an alkyloxycarbonyl group is most preferred. On the other hand, in the case where two or three $R^7$'s are bonded, the bonding position is preferably an ortho-position and/or a para-position. In particular, the case where n=1 is more preferred.

The aromatic tertiary amine compound represented by the above-mentioned general formula is illustrated specifically. Examples of the compound that is an alkyloxycarbonyl group in which $R^7$ is bonded to a para-position include methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, and propyl p-diethylaminobenzoate. Further, specific examples of the other aromatic amine compounds include N,N-dimethylaniline, N,N-dibenzylaniline, N,N-dimethyl-p-toluidine, N,N-diethyl-p-toluidine, N,N-di(β-hydroxyethyl)-p-toluidine, N,N,2,4,6-pentamethylaniline, N,N,2,4-tetramethylaniline, N,N-diethyl-2,4,6-trimethylaniline, N,N-dimethylacetophenone, N,N-dimethylcyanobenzene, p-dimethylaminobenzoic acid, and p-dimethylaminobenzoic acid amide. Of those, ethyl p-dimethylaminobenzoate or N,N-dimethyl-p-toluidine is particularly preferably used, and ethyl p-dimethylaminobenzoate is most preferred. A mixture of two or more kinds of those aromatic amine compounds may also be used.

The blending ratio of the aromatic amine compound in the filling/restoring material is preferably 0.05 to 5 parts by mass, more preferably 0.1 to 3 parts by mass with respect to 100 parts by mass of the polymerizable monomer having no acidic group because a too small blending ratio may lead to an insufficient effect of improving the polymerization activity of the photopolymerization initiator, and on the other hand, blending the aromatic amine compound at an excessive ratio is liable to cause a change in color in a cured body though the degree of the change is moderate compared with the aliphatic amine compound.

Photoacid Generator (iv)

The term "photoacid generator" refers herein to a compound having a function of generating an acid by irradiation of light. Any known photoacid generator can be used without any limitation as the photoacid generator. Specific examples thereof include an aryliodonium salt, a halomethyl group-substituted s-triazine derivative, a sulfonium salt compound, and a pyridinium salt compound. Of those photoacid generators, an aryliodonium salt and a halomethyl group-substituted s-triazine derivative can be suitably used because of their high polymerization initiating ability. In particular, an aryliodonium salt is more preferably used because of its good sunlight stability.

Examples of the diaryliodonium salt compound include chlorides, bromides, tetrafluoroborates, hexafluorophosphates, hexafluoroarsenates, hexafluoroantimonates, tetrakis(pentafluorophenyl)borates, and trifluoromethanesulfonates of diphenyliodonium, bis(p-chlorophenyl)iodonium, ditolyliodonium, bis(p-tert-butylphenyl)iodonium, bis(m-nitrophenyl)iodonium, p-tert-butylphenylphenyliodonium, methoxyphenylphenyliodonium, p-octyloxyphenylphenyliodonium, 4-isopropylphenyl-4-methylphenyliodonium, and the like. In particular, from the viewpoint of compound solubility, tetrafluoroborates, hexafluorophosphates, hexafluoroarsenates, hexafluoroantimonates, trifluoromethanesulfonates, and tetrakis(pentafluorophenyl)borates are preferably used.

Examples of the halomethyl group-substituted s-triazine derivative include
2,4,6-tris(trichloromethyl)-s-triazine,
2,4,6-tris(tribromomethyl)-s-triazine,
2-methyl-4,6-bis(trichloromethyl)-s-triazine,
2-methyl-4,6-bis(tribromomethyl)-s-triazine,
2-phenyl-4,6-bis(trichloromethyl)-s-triazine,
2-(p-methoxyphenyl)-4,6-bis(trichloromethyl)-s-triazine,
2-(p-methylthiophenyl)-4,6-bis(trichloromethyl)-s-triazine,
2-(p-chlorophenyl)-4,6-bis(trichloromethyl)-s-triazine,
2-(2,4-dichlorophenyl)-4,6-bis(trichloromethyl)-s-triazine,
2-(p-bromophenyl)-4,6-bis(trichloromethyl)-s-triazine,
2-(p-tolyl)-4,6-bis(trichloromethyl)-s-triazine,
2-n-propyl-4,6-bis(trichloromethyl)-s-triazine,
2-(α,α,β-trichloroethyl)-4,6-bis(trichloromethyl)-s-triazine,
2-styryl-4,6-bis(trichloromethyl)-s-triazine,
2-(p-methoxystyryl)-4,6-bis(trichloromethyl)-s-triazine,
s-(o-methoxystyryl-4,6-bis(trichloromethyl)-s-triazine,
s-(p-butoxystyryl)-4,6-bis(trichloromethyl)-s-triazine,
2-(3,4-dimethoxystyryl)-4,6-bis(trichloromethyl)-s-triazine, and
2-(3,4,5-trimethoxystyryl)-4,6-bis(trichloromethyl)-s-triazine.

A mixture of two or more kinds of the above-mentioned photoacid generators may also be used. In the filling/restoring repair material, although the blending amount of the photoacid generator is not particularly limited as long as the photoacid generator exhibits the effect, the blending amount is preferably 0.001 to 12 parts by mass, more preferably 0.005 to 6 parts by mass with respect to 100 parts by mass of the polymerizable monomer having no acidic group from the viewpoint of achieving a high polymerization activity.

(A) Filler (IV)

The filler contained in the filling/restoring material forming the dental filling/restoration kit according to this embodiment exerts the functions of improving the strength of a cured body and suppressing the contraction of the cured body at the time of its polymerization. It is possible to use appropriately, as such filler, one kind or more selected from an inorganic filler (the inorganic filler is an inorganic filler excluding a basic inorganic material), an organic filler, and an inorganic-organic composite filler.

Examples of the inorganic filler include quartz, silica, silica-titania, silica-zirconia, lanthanum glass, barium glass, and strontium glass. Note that some of those inorganic fillers have strongly acidic sites on their surfaces, and hence the above-mentioned aliphatic amine compound and aromatic amine compound may adsorb to the strongly acidic sites. Thus, it is preferred to use, as the inorganic filler, an inorganic filler that does not exhibit, in anhydrous toluene, a bluish-purple color induced by 4-phenylazodiphenylamine, which is a strongly basic indicator.

Here, although the measurement of the above-mentioned acidic sites using 4-phenylazodiphenylamine may be conducted in accordance with a routine procedure, the measurement is generally conducted by the following method. More specifically, first, a filler is dried at 100° C. for 3 or more hours and stored in a desicator containing diphosphorus pentoxide. 1 g of the resultant filler is placed in a sample tube, and then, 3 g of anhydrous toluene is placed, followed by shaking vigorously, whereby the filler is dispersed so as not to form an aggregate. After the dispersion, one drop (about 0.016 g) of a 0.004 mol/l anhydrous toluene solution of 4-phenylazodiphenylamine stored under shading is added to the sample tube, followed by shaking similarly, and thereafter, a bluish-purple color may be determined by visual inspection.

Examples of the organic filler which may be used include: non-crosslinkable polymers such as polymethyl(meth)acrylate, polyethyl(meth)acrylate, a methyl(meth)acrylate/ethyl (meth)acrylate copolymer, a methyl(meth)acrylate/butyl (meth)acrylate copolymer, and a methyl(meth)acrylate/styrene copolymer; and (meth)acrylate polymers such as a methyl (meth)acrylate/ethylene glycol di(meth)acrylate copolymer, a methyl(meth)acrylate/triethylene glycol di(meth)acrylate copolymer, and copolymers of methyl (meth)acrylate with a butadiene-based monomer.

In addition, an inorganic-organic composite filler may also be used preferably. For example, a polymerizable monomer is previously added to an inorganic filler to obtain a paste, and the paste is polymerized and crushed, whereby a particulate organic-inorganic composite filler can be obtained. As the organic-inorganic composite filler, for example, a TMPT filler (obtained by mixing trimethylolpropane methacrylate and a silica filler, followed by polymerization and crushing) or the like can be used.

When the above-mentioned filler is treated with a surface treatment agent typified by a silane coupling agent, the affinity with a polymerizable monomer having no acidic group, the dispersibility in the polymerizable monomer having no acidic group, and the mechanical strength and water resistance of a cured body can be enhanced. There is no particular limit to the surface treatment agent and the surface treatment method, and the same silane coupling agent as used in the surface treatment of the basic inorganic material described above may be adopted.

The refractive index of the above-mentioned filler is not particularly limited. Thus, for general dental applications, a filler having a refractive index in the range of 1.4 to 2.2 is used preferably. Further, there is no particular limit to the shape or the particle size. Although the shape or particle size is selected to be used appropriately, it is preferred that an average particle size be generally 0.001 to 100 μm, particularly 0.001 to 10 μm. Further, of the above-mentioned fillers, it is preferred to use a spherical filler, because the surface lubricative property of a cured body to be obtained increases to obtain an excellent restoring material.

The blending ratio of the filler in the filling/restoring material is preferably in the range of 80 to 2000 parts by mass with respect to 100 parts by mass of the polymerizable monomer having no acidic group, from the viewpoints of improving the strength of the cured body and suppressing the contraction of the cured body at the time of its polymerization and in view of the property that the viscosity (operability) of the filling/restoring material before curing can be adjusted depending on the blending ratio of the filler. The blending ratio of the filler is particularly preferably 90 to 500 parts by mass, most preferably 100 to 230 parts by mass with respect to 100 parts by mass of the polymerizable monomer having no acidic group.

In the filling/restoring material forming the dental filling/restoration kit according to this embodiment, it may be possible to use in combination a polymerization initiator other than the photopolymerization initiator including each component in the item (III). Examples of the other polymerization initiators include an aryl borate compound/acidic compound, an organic peroxide/amine compound, an azo compound/organic peroxide, an acylphosphine oxide compound, a thioxanthone compound, an α-aminoacetophenone compound, and a fused polycyclic aromatic compound. A fused polycyclic aromatic compound is particularly preferred because of its excellent curing rate. Any known fused polycyclic aromatic compound can be used as the fused polycyclic aromatic compound without any limitation. However, preferred is a fused polycyclic aromatic compound having the structure that a saturated carbon atom having at least one hydrogen atom is bonded to a fused polycyclic aromatic ring. More preferably used is a fused polycyclic aromatic compound having an anthracene ring. Specific examples thereof include 9,10-dimethylanthracene and 7,12-dimethyl[a]benzanthracene.

Further, it may be possible to add, in the filling/restoring material, a pigment, a fluorescent pigment, a dye, and an ultraviolet absorbing agent for preventing a color change caused by ultraviolet rays for the purpose of matching to the color tone of a tooth. Other known additives may be blended as components of the filling/restoring material in a content range in which the blend of the additives does not affect the effect of reducing the neutralization of the aliphatic amine compound.

In order to mix each component described above to produce the filling/restoring material, it is recommended to carry out the mixing in accordance with a known method of producing a filling/restoring material. In general, it is recommended that all components blended be weighed under red light and be mixed well until a homogeneous solution is formed.

[Adhesive Material (B)]

The adhesive material forming the dental filling/restoration kit according to this embodiment includes (I) a polymerizable monomer including a polymerizable monomer having an acidic group and (II) a polymerization initiator.

(B) Polymerizable Monomer Including Polymerizable Monomer (I) Having Acidic Group It is possible to use any polymerizable monomer having at least one acidic group in its molecule without any limitation as a polymerizable monomer having an acidic group contained in the adhesive material forming the dental filling/restoration kit according to this embodiment. Note that the acidic groups refer to the same ones mentioned in the description about the polymerizable monomer having no acidic group. Of those acidic groups, a carboxyl group, a phosphate monoester group, or a phosphate diester group is more preferred as an acidic group highly adhesive to a tooth.

As described above, the adhesive material includes the polymerizable monomer having an acidic group. On the other hand, as described previously, the filling/restoring material which is filled on the cured layer of the adhesive material includes an aliphatic amine compound and an aromatic amine compound as components of the photopolymerization initiator, and the filling/restoring material also includes a basic inorganic material. The basic inorganic material neutralizes an acidic group owned by each polymerizable monomer having an acidic group in the above-mentioned adhesive material competitively or preferentially, and hence the polymerization activity of the filling/restoring material is maintained favorably at the contact interface of both materials.

The effect of the polymerizable monomer having an acidic group on highly maintaining the polymerization activity of the filling/restoring material is remarkably exerted when the acidic group owned by the polymerizable monomer having an acidic group is strongly acidic. Specifically, the effect is suitably exerted when a polymerizable monomer having an acidic group with a pKa value of 2.15 or less in water at 25° C. is included in the adhesive material. That is, a strongly acidic group intrinsically has a high demineralizing ability and is excellent in adhesiveness to a tooth. However, on the other hand, the strongly acidic group has a strong neutralization action on an aliphatic amine compound. Thus, when an adhesive material including this polymerizable monomer having a strongly acidic group is used with the filling/restoring material including the photopolymerization initiator formed by combining an α-diketone compound, an aliphatic amine compound, an aromatic amine compound, and a photoacid generator, the high polymerization activating ability of the photopolymerization initiator is significantly reduced. However, when the dental filling/restoration kit according to this embodiment is used, the basic inorganic material neutralizes a strongly acidic group owned by the polymerizable monomer having a strongly acidic group competitively or preferentially. Thus, the polymerization activating ability of the photopolymerization initiator is not reduced by the neutralization reaction with the strongly acidic group, and its original polymerization activating ability can be sufficiently exerted. As a result, the adhesive strength can be further enhanced by the high adhesiveness to a tooth attributed to the strongly acidic group and the polymerization activating ability owned by the above-mentioned photopolymerization initiator.

As the strongly acidic group, a phosphate acidic group is more preferred because it is particularly excellent in affinity to a tooth. The phosphate acidic group is a group of acidic groups each having a —P(=O) (OH)— group derived from phosphoric acid. Specific examples of the phosphate acidic group include a phosphinic acid group, a phosphonic acid group, a hydrogen phosphonate monoester group, a dihydrogen phosphate monoester group, and a hydrogen phosphate diester group. Of those, a dihydrogen phosphate monoester group or a hydrogen phosphate diester group is most preferred.

Examples of the polymerizable monomer having an acidic group that contains a dihydrogen phosphate monoester group or a hydrogen phosphate diester group include 2-(meth)acryloyloxyethylphenyl hydrogen phosphate, bis((meth)acryloyloxyethyl)hydrogen phosphate, (meth) acryloyloxyethyl dihydrogen phosphate, 10-(meth)acryloyloxydecyl dihydrogen phosphate, and 6-(meth)acryloyloxyhexyl dihydrogen phosphate.

Further, examples of the polymerizable monomer having an acidic group that contains a phosphinic acid group include bis(2-methacryloxy)phosphonic acid, bis(methacryloxypropyl)phosphinic acid, and bis(methacryloxybutyl)phosphinic acid. Examples of the polymerizable monomer having an acidic group that contains a phosphonic acid group include 3-methacryloxypropylphosphonic acid, 2-methacryloxyethoxycarbonylmethylphosphonic acid, 4-methacryloxybutoxycarbonylmethylphosphonic acid, 6-methacryloxyhexyloxycarbonylmethylphosphonic acid, and 2-(2-ethoxycarbonylallyloxy)ethylphosphonic acid. In addition, examples of the polymerizable monomer having an acidic group that contains a hydrogen phosphonate monoester group include 2-methacryloxyethylphosphonic acid mono(methacryloxyethyl)ester and 2-methacryloxyethylphosphonic acid monophenyl ester.

More specific examples of the polymerizable monomer having an acidic group that may be suitably used in the dental filling restoration kit according to this embodiment include: polymerizable monomers each having a carboxylic acid acidic group such as 11-methacryloyloxy-1,1-undecanedicarboxylic acid, 2-(meth)acryloyloxyethyl hydrogen maleate, 2-(meth)acryloyloxyethyl hydrogen succinate, 2-(meth)acryloyloxyethyl hydrogen phthalate, 11-(meth)acryloyloxyethyl-1,1-undecanedicarboxylic acid, 2-(meth)acryloyloxyethyl-3'-methacryloyloxy-2'-(3,4-dicarboxybenzoyloxy)propyl succinate, 4-(2-(meth)acryloyloxyethyl)trimellitate anhydride, N-(meth) acryloylglycine, and N-(meth)acryloylaspartic acid; polymerizable monomers each having a phosphonic acid acidic group such as vinyl phosphonate; and polymerizable monomers each having a sulfonic acid group such as styrenesulfonic acid, 3-sulfopropan(meth)acrylate, and 2-(meth)acrylamide-2-methylpropanesulfonic acid. Further, two kinds or more of those polymerizable monomers each having an acidic group may be used in combination if necessary.

In the adhesive material forming the dental filling/restoration kit according to this embodiment, such polymerizable monomer having an acidic group may be blended so as to account for the whole polymerizable monomer blended. However, if the adjustment of physical properties of the adhesive material as described below is required or too many acidic groups are included in the adhesive material, the effect of suppressing the activity reduction of an aliphatic amine compound in the filling/restoring material may become insufficient, and hence a polymerizable monomer having no acidic group may be used together as another polymerizable monomer. From the viewpoint of sufficiently strengthening the adhesiveness of the adhesive material to a tooth, the polymerizable monomer having an acidic group is preferably blended at 5 to 50 parts by mass in 100 parts by mass of the whole polymerizable monomer included in the adhesive material. The polymerizable monomer having an acidic group is desirably contained more preferably at 10 to 30 parts by mass in 100 parts by mass of the above-mentioned polymerizable monomer.

Note that it is preferred that a water-soluble polymerizable monomer and a water-insoluble polymerizable monomer both described below be used, as the polymerizable monomer having no acidic group, differently for each physical property required. That is, using the water-insoluble polymerizable monomer is preferred because the mechanical strength of the adhesive material becomes higher. On the other hand, using the water-soluble polymerizable monomer is preferred because the permeability of the adhesive material into a tooth can be improved and the compatibility of the water-insoluble polymerizable monomer with water can be improved. For example, when an adhesive material containing the above-mentioned water-insoluble polymerizable monomer coexists with water, phase separation sometimes occurs. In order to prevent the phase separation, it is preferred that a water-soluble polymerizable monomer such as 2-hydroxyethyl methacrylate be used in combination.

(B) Polymerization Initiator (II)

The polymerization initiator included in the adhesive material in the dental filling/restoration kit according to this embodiment is not particularly limited, and a chemical polymerization initiator can also be used favorably. However, a photopolymerization initiator is preferably used from the viewpoint of good operability, for example, not requiring cumbersome works such as heating a polymerization initiator and mixing two or more materials packed differently as in a redox system just before their use.

Examples of such photopolymerization initiator include: α-diketones (specific examples thereof are the same as those described for the component i) of the filling restoring material (A)); benzoin alkyl ethers such as benzoin methyl ether, benzoin ethyl ether, and benzoin propyl ether; thioxanthone derivatives such as 2,4-diethoxythioxanthone, 2-chlorothioxanthone, and methylthioxanthone; benzophenone derivatives such as benzophenone, p,p'-dimethylaminobenzophenone, and p,p'-methoxybenzophenone; acylphosphinoxide derivatives such as 2,4,6-trimethylbenzoyldiphenylphosphinoxide, bis(2,6-dimethoxybenzoyl)-2,4,6-trimethylbenzoyldiphenylphosphinoxide, bis(2,6-dimethoxybenzoyl)-2,4,4-trimethylpentylphosphinoxide, and bis(2,4,6-trimethylbenzoyl)phenylphosphinoxide; and photopolymerization initiators each formed of a system that combines an aryl borate compound, a coloring matter, and a photoacid generator.

Of the above-mentioned α-diketones, camphorquinone and benzil are preferred. Further, of the acylphosphinoxides, 2,4,6-trimethylbenzoyldiphenylphosphinoxide, bis(2,6-dimethoxybenzoyl)-2,4,4-trimethylpentylphosphinoxide, and bis(2,4,6-trimethylbenzoyl)phenylphosphinoxide are preferred.

Note that any of those α-diketones and acylphosphine oxides solely exhibits a photopolymerization activity, but it is preferred to use it together with an aromatic amine compound such as ethyl 4-(dimethylamino)benzoate or lauryl 4-(dimethylamino)benzoate, because a higher activity is provided. Note that, the aromatic amine compound is a weakly basic compound as describe above, and hence, even when the aromatic amine compound is used, as a component of such photopolymerization initiator, for the curing of a polymerizable composition including a polymerizable monomer having an acidic group, the aromatic amine compound exerts a sufficient polymerization activity.

Further, there are preferably used, as an aryl borate compound/coloring matter/photoacid generator-based photopolymerization initiator, a photopolymerization initiator that is disclosed in JP 09-3109 A or the like. More specifically, there is particularly preferably used a photopolymerization initiator formed by using an aryl borate compound such as a tetraphenylboron sodium salt, a coumarin-based coloring matter such as 3,3'-carbonylbis(7-diethylamino) coumarin or 3,3'-carbonylbis(4-cyano-7-diethylaminocoumarin) as a coloring matter, and a halomethyl group-substituted s-triazine derivative such as 2,4,6-tris(trichloromethyl)-s-triazine or a diphenyliodonium salt compound as a photoacid generator.

Not only the each photopolymerization initiator can be solely blended, but also a plurality kinds of the photopolymerization initiators can be blended in combination if necessary. The blending ratio of those polymerization initiators is generally in the range of 0.01 to 30 parts by mass, more preferably in the range of 0.1 to 20 parts by mass with respect to 100 parts by mass of the whole polymerizable monomer contained in the adhesive material. Further, it is recommended that each blending ratio of the aryl borate compound/coloring matter/photoacid generator-based photopolymerization initiator be controlled to 0.01 to 15 parts by mass of an aryl borate compound, 0.001 to 5 parts by mass of a coloring matter, and 0.01 to 10 parts by mass of a photoacid generator, with respect to 100 parts by mass of a polymerizable monomer.

Note that, when a chemical polymerization initiator is used as a polymerization initiator in the dental filling/restoration kit according to this embodiment, there can be preferably used a redox-system polymerization initiator that causes radicals to occur by combining two or more kinds of compounds. Exemplified as a typical redox-system chemical polymerization initiator is a system formed of aryl borates and an acidic compound or a system formed of a barbituric acid derivative, a copper compound, and a halogen compound. Here, a chemical polymerization initiator including an aromatic amine compound as its component, such as a peroxide/aromatic amine compound system, causes a chemical polymerization reaction to progress gently, and the reaction in which the aromatic amine compound is involved is reversible. Thus, the chemical polymerization initiator does not sufficiently function in the curing reaction of a polymerizable composition including a polymerizable monomer having an acidic group. Therefore, when a chemical polymerization initiator is used as a polymerization initiator, it is preferred to use such chemical polymerization initiator including an aromatic amine compound as its component as least as possible.

The blending ratio of each of those chemical polymerization initiators is not limited, either, as long as the blending ratio is in a content range in which the effect of reducing the neutralization of an aliphatic amine compound is not blocked and the blending ratio is an effective ratio (in general, as in the case of the photopolymerization initiator, preferably 0.01 to 30 parts by mass, more preferably 0.1 to 20 parts by mass with respect to 100 parts by mass of the whole polymerizable monomer included in an adhesive material).

Further, the adhesive material forming the dental filling/restoration kit according to this embodiment may include water in order to assist demineralization of a tooth. In particular, including water is preferred, because a tooth demineralizing ability is imparted to the adhesive material, leading to elimination of a pretreatment agent and resulting in being able to provide a one-step adhesive material. Further, after the adhesive material is applied on the surface of a tooth, most water is evaporated by air blowing or the like. However, when the basic inorganic material included in the filling/restoring material is a basic inorganic material eluting metal ions, such as fluoroaluminosilicate glass, the balance of water functions to elute metal ions, and hence including water is preferred. The content of water is preferably 3 to 50 parts by mass, particularly preferably 10 to 25 parts by mass, most preferably 12 to 20 parts by mass with respect to 100 parts by mass of the whole polymerizable monomer included in the adhesive material.

In addition, the adhesive material may include a hydrophilic organic solvent having fluidity in order to further improve its operability. The adhesive material may include a solvent such as acetone, ethanol, isopropyl alcohol, or tertiary butanol. A solvent being highly volatile and being less toxic, such as acetone, ethanol, or isopropyl alcohol, is particularly preferably used because the drying described below is facilitated. The content of the hydrophilic organic solvent is preferably 20 to 400 parts by mass, more preferably 50 to 300 parts by mass with respect to 100 parts by mass of the whole polymerizable monomer included in the adhesive material.

In addition, the adhesive material may include a filler in order to enhance the strength of the cured layer. Specifically, the same fillers as those described in the filling/restoring material (A) mentioned above can be used favorably. Of those, fluoroaluminosilicate glass, which is an ion-eluting filler, is preferably used. The fluoroaluminosilicate glass used here needs to be added in a content range in which the acidity of the acidic group of the polymerizable monomer having an acidic group is not seriously impaired and in which the effect of reducing the neutralization of the aliphatic amine compound is significantly exerted. Specifically, preferred is the content range that is effective for retaining the pH at 25° C. of the adhesive material to 2.5 or less. More specifically, it is favorable to suppress the ratio of the total valence of ions of a basic compound to the total valence of acids of acidic groups owned by the polymerizable monomers having an acidic group to 0.8 or less, more preferably 0.7 or less.

Besides, it is possible to add, to the adhesive material, a polymer compound such as polyvinyl pyrrolidone, carboxymethyl cellulose, or polyvinyl alcohol as an organic thickener in a content range in which the performance of the adhesive material is not lowered. Further, various kinds of additives such as an ultraviolet absorbing agent, a dye, an antistatic agent, a pigment, and a fragrance can be selectively used if necessary. Further, an amine compound may be added for an action as a pH adjuster or the like. The each component described above is mixed in one liquid to serve as an adhesive material. As far as its form in storage concerned, one liquid is preferred from the viewpoint of easy handling. However, for example, when a chemical polymerization initiator is used, it is acceptable to adopt the form that two or more liquids are packed differently and are mixed into one liquid for use. In order to mix the two or more liquids, it is recommended to carry out the mixing in accordance with a known method of producing a dental adhesive material. In general, it is recommended that all components blended be weighed under red light and be mixed well until a homogeneous solution is formed.

Next, a method of using the dental filling/restoration kit according to this embodiment is described. In general, an adhesive material has good fluidity, and hence, first, the adhesive material is usually applied in the form that it is applied onto a tooth a plurality of times with a brush, a spatula, a paint brush, a roller, or the like, but the adhesive material may be applied onto a tooth surface by spraying. When an etchant needs to be used separately, pretreatment may be carried out beforehand.

After the adhesive material is applied or sprayed to the cavity, the adhesive material is preferably dried so as to evaporate most of excess water and organic solvent. Examples of the drying method include natural drying, heat drying, blast drying, drying under reduced pressure, and a combination thereof. Of those, considering drying the adhesive material in the mouth, blast drying (for approximately 3 to 20 seconds) with the use of an air gun sending dried air is preferred.

The adhesive material is dried as described above, and the filling/restoring material is mounted on the cured adhesive material to fill the cavity. At this time, a method of using the filling/restoring material is not particularly limited. In general, the filling/restoring material is mounted with a spatula or the like, and is formed into a shape similar to the actual tooth. Finally, the filling/restoring portion is irradiated with visible light with a dental light irradiator, thereby being able to cure the filling/restoring material.

EXAMPLES

Hereinafter, the dental filling/restoration kit of the present invention is described specifically based on examples, but the present invention is not limited to these examples. Note that abbreviated names and abbreviated codes shown in the examples and comparative examples refer to the following.

[Polymerizable Monomer Having No Acidic Group]
D-2.6E: 2,2'-bis[4-(methacryloxyethoxy)phenyl]propane
Bis-GMA: 2,2'-bis[4-(2-hydroxy-3-methacryloxypropoxy)phenyl]propane
3G: triethylene glycol dimethacrylate
HEMA: 2-hydroxyethyl methacrylate
UDMA: urethane dimethacrylate
[Polymerizable Monomer Having Acidic Group]
PM: a mixture in which 2-methacryloyloxyethyl dihydrogen phosphate and bis(2-methacryloyloxyethyl)hydrogen phosphate are mixed at a mass ratio of 2:1
MDP: 10-methacryloxydecyl dihydrogen phosphate
MAC-10: 11,11-dicarboxyundecyl methacrylate
[Volatile Water-Soluble Organic Solvent]
IPA: isopropyl alcohol
AN: acetone
[Aliphatic Amine Compound]
DMEM: N,N-dimethylaminoethyl methacrylate
TEOA: triethanolamine
MDEOA: N-methyldiethanolamine
[Aromatic Amine Compound]
DMPT: N-dimethyl-p-toluidine
DMBE: ethyl p-N,N-dimethylaminobenzoate
[Aryliodonium Salt]
DPI: diphenyliodonium hexafluorophosphate
DPIB: 4-methylphenyl-4'-isopropylphenyliodonium tetrakis(pentafluorophenyl)borate
[Triazine Derivative]
TCT: 2,4,6-tris(trichloromethyl)-s-triazine
PBCT: 2-phenyl-4,6-bis(trichloromethyl)-s-triazine
[α-Diketone Compound]
BZ: benzil
CQ: camphorquinone
[Polymerization Inhibitor]
HQME: hydroquinone monomethyl ether
BHT: 2,6-di-t-butyl-p-cresol
[Basic Inorganic Material]
AO: alumina powder (average particle size: 0.02 μm, specific surface area: 100 $m^2/g$)
NaF: sodium fluoride (average particle size: 4.0 μm, specific surface area: 2 $m^2/g$)
CS: calcium silicate (average particle size: 5.0 μm, specific surface area: 2 $m^2/g$)
MF1: a product obtained by crushing fluoroaluminosilicate glass powder (TOKUSO IONOMER, manufactured by Tokuyama Corporation) so as to have an average particle size of 0.5 μm by using a wet-type continuous ball mill (NEW MY MILL, manufactured by Mitsui Mining Co., Ltd.), and then carrying out modification treatment on the surfaces of fillers with 20 g of 5.0 N hydrochloric acid with respect to 1 g of the crushed powder for 20 minutes (average particle size: 0.5 μm, 24-hour elution ion amount: 27 meq/g filler, specific surface area: 40 $m^2/g$)
MF2: a product obtained by crushing fluoroaluminosilicate glass powder (TOKUSO IONOMER, manufactured by Tokuyama Corporation) so as to have an average particle size of 1.5 μm by using the above-mentioned wet-type continuous ball mill, and then carrying out modification treatment on the surfaces of fillers with 20 g of 5.0N hydrochloric acid with respect to 1 g of the crushed powder for 20 minutes (average particle size: 1.5 μm, 24-hour elution ion amount: 20 meq/g filler, specific surface area: 20 m²/g)

MF3: a product obtained by crushing fluoroaluminosilicate glass powder (TOKUSO IONOMER, manufactured by Tokuyama Corporation) so as to have an average particle size of 3.0 μm by using the above-mentioned wet-type continuous ball mill, and then carrying out modification treatment on the surfaces of fillers with 20 g of 5.0 N hydrochloric acid with respect to 1 g of the crushed powder for 20 minutes (average particle size: 4.0 μm, 24-hour elution ion amount: 8 meq/g of filler, specific surface area: 1 m²/g).

[Filler]
F1: a mixture obtained by mixing spherical silica-zirconia (average particle size: 0.4 μm) hydrophobized with γ-methacryloyloxypropyl trimethoxysilane with spherical silica-titania (average particle size: 0.08 μm) hydrophobized with γ-methacryloyloxypropyl trimethoxysilane in a mass ratio of 70:30

[Ultraviolet Absorbing Agent]
BS: 2-hydroxy-4-methoxybenzophenone

[Acylphosphine Oxide]
TPO: 2,4,6-trimethylbenzoyl diphenylphosphine oxide

[Borate Salt]
PhB-TEOA: tetraphenylborate triethanolamine salt

[Peroxide]
HP: 1,1,3,3-tetramethylbutylhydroperoxide

[Polymer]
PMMA: polymethyl methacrylate

Further, each measurement of various physical properties was performed in the examples and the comparative examples in accordance with the following methods.

(1) Measurement of Basicity of Basic Inorganic Material

Phosphoric acid was dropped to a solution in which distilled water and ethanol were mixed in a volume ratio of 1:1, and the pH of the resultant solution was adjusted to 2.50 through measurement with a pH meter (main body: ion meter IM 20E, electrode: GST-5721S, both of which were manufactured by DKK-TOA Corporation) at 23° C., yielding a dispersion medium for measurement. 20 g of the dispersion solution and 1.0 g of a basic inorganic material were fed into a beaker having a base area of 706.5 mm² in its inner space portion, and the whole was stirred at 23° C. for 2 minutes at a rotation number of 200 rpm by using a stirrer with a diameter of 8 mm and a length of 20 mm. Immediately after the stirring for 2 minutes, the pH of the dispersion was measured with a pH meter soaked in the dispersion. The value obtained by subtracting the pH value of the dispersion medium from the pH value of the dispersion after the stirring was defined as a pH difference. Table 1 shows measurement values and pH differences in various kinds of basic inorganic materials used in the examples and comparative examples.

(2) Method of Measuring Eluted Ions of Basic Inorganic Material 0.2 g of the dispersion was weighed in a 100-ml sample tube, and diluted to 1% by mass using IPA. The solution thus obtained was filtered with a syringe filter, and the presence or absence of the elution of metal ions was checked by subjecting the filtrate to an inductively coupled plasma (ICP) emission spectral analysis. The measured value and pH difference of each of the basic inorganic materials used in the examples and comparative examples are as shown in Table 1.

TABLE 1

|  | Dispersion pH | pH difference | Eluted metal ions |
|---|---|---|---|
| AO | 2.58 | 0.08 | None |
| FNa | 5.36 | 2.86 | $Na^+$ |
| CS | 8.08 | 5.58 | $Ca^{2+}$ |
| MF | 2.71 | 0.21 | $Al^{3+}$, $La^{3+}$ |

(3) Preparation of Composite Resin

With respect to 7.0 g of D-2.6E, 2.0 g of 3G, and 1.0 g of UDMA, 0.05 g of DBME, 0.05 g of MDEOA, 0.03 g of CQ, 0.075 g of DPIB, 0.015 g of HQME, 0.002 g of BHT, and 0.2 g of BS were added, and the mixture was stirred until it became homogeneous in a dark room to obtain a matrix. The obtained matrix was mixed with 20.9 g of F1 and 0.8 g of MF1 in an agate mortar, and deaerated under vacuum, whereby a filling/restoring material CR1 with a filler filling ratio of 68.0% was obtained. Other composite resins (CR2 to CR18) were also produced in the compositions shown in Tables 2 and 3 in the same procedure.

TABLE 2

| | Composition of composite resin (part(s) by mass) | | | | | | | | | | | |
|---|---|---|---|---|---|---|---|---|---|---|---|---|
| | Polymerizable monomer having no acidic group | | | | Basic inorganic material | | | | α-Diketone compound | Aliphatic amine | | |
| | Bis- | | | | | | | | | | | |
| | D-2.6E | GMA | 3G | UDMA | MF1 | AO | NaF | CS | CQ | MDEOA | DMEM | TEOA |
| CR1 | 70 |  | 20 | 10 | 15 |  |  |  | 0.3 | 0.5 |  |  |
| CR2 | 70 |  | 20 | 10 |  | 15 |  |  | 0.3 | 0.5 |  |  |
| CR3 | 70 |  | 20 | 10 |  |  | 15 |  | 0.3 | 0.5 |  |  |
| CR4 | 70 |  | 20 | 10 |  |  |  | 15 | 0.3 | 0.5 |  |  |
| CR5 | 70 |  | 20 | 10 | 3 |  |  |  | 0.3 | 0.5 |  |  |
| CR6 | 70 |  | 20 | 10 | 7 |  |  |  | 0.3 | 0.5 |  |  |
| CR7 | 70 |  | 20 | 10 | 75 |  |  |  | 0.3 | 0.5 |  |  |
| CR8 | 70 |  | 20 | 10 |  |  |  |  | 0.3 | 0.5 |  |  |
| CR9 | 70 |  | 20 | 10 | 15 |  |  |  | 0.3 |  | 0.5 |  |
| CR10 | 70 |  | 20 | 10 | 15 |  |  |  | 0.3 |  |  | 0.5 |

TABLE 2-continued

| | | Composition of composite resin (part(s) by mass) | | | | | | |
|---|---|---|---|---|---|---|---|---|
| | | Aromatic amine | | Photoacid generator | | | | Filler |
| | | DMBE | DMPT | DPIB | DPI | TCT | PBCT | F1 |
| | CR1 | 0.5 | | 0.75 | | | | 202 |
| | CR2 | 0.5 | | 0.75 | | | | 202 |
| | CR3 | 0.5 | | 0.75 | | | | 202 |
| | CR4 | 0.5 | | 0.75 | | | | 202 |
| | CR5 | 0.5 | | 0.75 | | | | 214 |
| | CR6 | 0.5 | | 0.75 | | | | 210 |
| | CR7 | 0.5 | | 0.75 | | | | 137 |
| | CR8 | 0.5 | | 0.75 | | | | 217 |
| | CR9 | 0.5 | | 0.75 | | | | 202 |
| | CR10 | 0.5 | | 0.75 | | | | 202 |

Other added components common to CR1 to CR10
Polymerization inhibitor: HQME = 0.15 (part by mass), BHT = 0.02 (part by mass), Ultraviolet absorbing agent: BS = 2.0 (parts by mass)

TABLE 3

| | Composition of composite resin (part(s) by mass) | | | | | | | | | | |
|---|---|---|---|---|---|---|---|---|---|---|---|
| | Polymerizable monomer having no acidic group | | | | Basic inorganic material | | | α-Diketone compound | Aliphatic amine | | |
| | Bis- | | | | | | | | | | |
| | D-2.6E | GMA | 3G | UDMA | MF1 | MF2 | MF3 | CQ | MDEOA | DMEM | TEOA |
| CR11 | 70 | | 20 | 10 | 15 | | | 0.3 | 0.1 | | |
| CR12 | 70 | | 20 | 10 | 15 | | | 0.3 | 4 | | |
| CR13 | 70 | | 20 | 10 | 15 | | | 0.3 | 2.5 | | |
| CR14 | 70 | | 20 | 10 | 15 | | | 0.3 | | | |
| CR15 | 70 | | 20 | 10 | | | | 0.3 | | | |
| CR16 | 70 | | 20 | 10 | 15 | | | 0.3 | 0.5 | | |
| CR17 | 70 | | 20 | 10 | 15 | | | 0.3 | 0.5 | | |
| CR18 | 70 | | 20 | 10 | 15 | | | 0.3 | 0.5 | | |
| CR19 | | 60 | 40 | | 15 | | | 0.3 | 0.5 | | |
| CR20 | 70 | | 20 | 10 | 15 | | | 0.3 | 0.5 | | |
| CR21 | 70 | | 20 | 10 | 15 | | | 0.3 | 0.5 | | |
| CR22 | 70 | | 20 | 10 | 15 | | | 0.3 | 0.5 | | |
| CR23 | 70 | | 20 | 10 | | 15 | | 0.3 | 0.5 | | |
| CR24 | 70 | | 20 | 10 | | | 15 | 0.3 | 0.5 | | |

| | | Composition of composite resin (part(s) by mass) | | | | | | |
|---|---|---|---|---|---|---|---|---|
| | | Aromatic amine | | Photoacid generator | | | | Filler |
| | | DMBE | DMPT | DPIB | DPI | TCT | PBCT | F1 |
| | CR11 | 0.5 | | 0.75 | | | | 201 |
| | CR12 | 0.5 | | 0.75 | | | | 209 |
| | CR13 | 0.5 | | 0.75 | | | | 209 |
| | CR14 | 0.5 | | 0.75 | | | | 201 |
| | CR15 | 0.5 | | 0.75 | | | | 216 |
| | CR16 | | 0.5 | 0.75 | | | | 202 |
| | CR17 | 0.1 | | 0.75 | | | | 201 |
| | CR18 | | | 0.75 | | | | 201 |
| | CR19 | 0.5 | | 0.75 | | | | 202 |
| | CR20 | 0.5 | | | 0.75 | | | 202 |
| | CR21 | 0.5 | | | | 0.75 | | 202 |
| | CR22 | 0.5 | | | | | 0.75 | 202 |
| | CR23 | 0.5 | | 0.75 | | | | 202 |
| | CR24 | 0.5 | | 0.75 | | | | 202 |

Other added components common to CR11 to CR24
Polymerization inhibitor: HQME = 0.15 (part by mass), BHT = 0.02 (part by mass), Ultraviolet absorbing agent: BS = 2.0 (parts by mass)

(4) Preparation of Adhesive Material (Including Photopolymerization Initiator as Polymerization Initiator)

2.5 g of PM, 3.0 g of Bis-GMA, 2.0 g of 3G, 2.5 g of HEMA, 1.0 g of MF1, 1.5 g of water, 8.5 g of IPA, 0.1 g of CQ, and 0.15 g of DMBE were weighed, and the whole was mixed in a dark place, yielding an adhesive material B1. Other adhesive materials (B2 to B7) were produced in the compositions shown in Table 4 in the same procedure.

TABLE 4

| | Composition of adhesive material (part(s) by mass) | | | | | | | | | | | | |
|---|---|---|---|---|---|---|---|---|---|---|---|---|---|
| Polymerizable monomer having acidic group | | | Polymerizable monomer having no acidic group | | | | Filler | Water | Water-soluble organic solvent | | Photopolymerization initiator | | |
| | | | Bis-GMA | | | | | | | | | | |
| PM | MDP | MAC-10 | GMA | D-2.6E | 3G | HEMA | MF | H$_2$O | AN | IPA | CQ | TPO | DMBE |
| B1 | 25 | | | 30 | | 20 | 25 | 10 | 15 | | 85 | 1.0 | | 1.5 |
| B2 | 25 | | | 30 | | 20 | 25 | 10 | 15 | | 85 | | 1.0 | |
| B3 | 25 | | | 30 | | 20 | 25 | 10 | 15 | 85 | | 1.0 | | 1.5 |
| B4 | 15 | | | | 50 | | 35 | 10 | 15 | 85 | | 1.0 | | 1.5 |
| B5 | | 15 | | | 50 | | 35 | 10 | 15 | 85 | | 1.0 | | 1.5 |
| B6 | 70 | | | 5 | | | 25 | 10 | 15 | 85 | | 1.0 | | 1.5 |
| B7 | | | 25 | 30 | | 20 | 25 | 10 | 15 | | 85 | 1.0 | | 1.5 |

Example 1 and Comparative Example 1

The combination of the adhesive material B1 and the composite resin CR1 was used to form dental filling/restoration kit for Example 1. The combination of the adhesive material B1 and the composite resin CR8 was used to form dental filling/restoration kit for Comparative Example 1. The following adhesive strength measurement test was carried out on each dental filling/restoration kit. Further, the following sunlight stability test was carried out on each composite resin. Table 5 and Table 6 shows each result.

<Adhesive Strength Measurement Test>

A cow was killed, and a foretooth of the cow was extracted within 24 hours after the killing. The extracted cow's foretooth was polished with emery paper #600 under water injection, and enamel and dentin flat surfaces were cut out so as to be parallel to the labial surface and flat. Next, the flat surfaces thus cut out were sprayed with compressed air for about 10 seconds and dried. Then, a double-sided tape having a hole with a diameter of 3 mm was attached to each of the flat surfaces, and paraffin wax having a hole with a thickness of 1.0 mm and a diameter of 8 mm was fixed with the center of the hole of the paraffin wax being aligned with the center of the hole of the double-sided tape attached previously, whereby a pseudo cavity was formed. An adhesive material was applied to the pseudo cavity and left to stand for 20 seconds. Then, the adhesive material was dried by blowing of compressed air for about 10 seconds and irradiated with visible light by a visible light irradiator (TOKUSO POWER LIGHT, manufactured by Tokuyama Corporation) for 10 seconds. Further, the resultant cavity was filled with a composite resin and irradiated with visible light by a visible light irradiator for 3 or 10 seconds, whereby an adhesive test chip in which the thickness of the composite resin was 1.0 mm was produced.

The above-mentioned adhesive test chip was soaked in water at 37° C. for 24 hours, and thereafter, was stretched at a cross-head speed of 2 mm/min, using a tensile tester (AUTOGRAPH, manufactured by Shimadzu Corporation), whereby the tensile adhesion strength between the tooth and the composite resin was measured. The tensile adhesion strength between the tooth and the composite resin was measured respectively for four test chips of various kinds in each example or each comparative example. The average value of four measurements for the tensile adhesion strength was used as the adhesive strength.

<Sunlight Stability of Composite Resin>

A composite resin was filled in a mold with which a disk-like test chip with a diameter of 15±1 mm and a thickness of 0.5±0.1 mm can be produced, followed by pressure bonding with a polypropylene film. Light irradiation was carried out for 10 seconds each on five sites with a visible light irradiator (TOKUSO POWER LIGHT, manufactured by Tokuyama Corporation) so that the whole composite resin was irradiated with light. A half part of the test chip was covered with an aluminum foil and was directly exposed to sunlight for 3 hours in total. The aluminum foil was removed and the test chip was stored for 5 hours in a dark place. A difference in color tone between an exposed portion and an unexposed portion was confirmed by visual observation.

Double Circle Mark . . . No difference in color tone between an exposed portion and an unexposed portion is found.
Single Circle Mark . . . A difference in color tone between an exposed portion and an unexposed portion is slightly remarkable.
Triangle Mark . . . A difference in color tone between an exposed portion and an unexposed portion is remarkable.
Cross Mark . . . A difference in color tone between an exposed portion and an unexposed portion is very remarkable.

In Example 1 carried out by combining the adhesive material B1 including a polymerizable monomer having an acidic group as a polymerizable monomer, and the composite resin CR1 including a polymerizable monomer having no acidic group, a system formed by combining an α-diketone compound, an aliphatic amine compound, an aromatic amine compound, and a photoacid generator as a photopolymerization initiator, and a basic inorganic material, high adhesive strength was provided with respect to an enamel and a dentin by visible light irradiation for both 10 seconds and 3 seconds. Further, the sunlight stability of the composite resin was excellent.

On the other hand, in Comparative Example 1 carried out in the same manner by using, as a composite resin, CR8 which had the same composition except not including a basic inorganic material, fairly good adhesive strength was provided with respect to an enamel and a dentin by visible light irradiation for 10 seconds, but adhesive strength with respect to the both by visible light irradiation for 3 seconds was found to be rather low.

Reference Example 1

An adhesive strength measurement test was carried out on the dental filling/restoration kit (adhesive material B1, composite resin CR8) used in Comparative Example 1 in the form that the adhesive material was applied in a pseudo cavity and dried, a polypropylene film was press-bonded on the surface of the adhesive material so as to form the state that the surface was sealed from air, visible light was irradiated to form a cured layer, and the composite resin was cured on the cured layer. In the case of this form, the polymerization reaction of the adhesive material progresses without undergoing the blocking of oxygen molecules in air, and hence no surface unpolymerized layer is substantially present in the cured surface of the adhesive material.

According to the results, visible light irradiation for 10 seconds exhibited an adhesive strength of 21.1 (2.5) MPa with respect to an enamel and an adhesive strength of 20.9 (2.0) MPa with respect to a dentin, and visible light irradiation for 3 seconds exhibited an adhesive strength of 20.8 (2.1) MPa with respect to an enamel and an adhesive strength of 20.1 (2.5) MPa with respect to a dentin. That is, the visible light irradiation for 3 seconds in Comparative Example 1 exhibited an adhesive strength having a low value with respect to both portions, but when an adhesive strength measurement test was carried out in the form that the polymerization reaction of the adhesive material was performed without undergoing the blocking of oxygen molecules in air (i.e., a surface unpolymerized layer was prevented from being formed in a cured surface), the adhesive strength was significantly improved. Each of those values was almost the same high level as each measurement result in Example 1 in which an adhesive strength measurement test was carried out by using the composite resin CR1, which had the same composition as a composite resin produced by blending a basic inorganic material in CR8.

From the results described above, it was able to be confirmed that the reduction in adhesive strength with respect to a tooth after visible light irradiation for 3 seconds in Comparative Example 1 was attributed to the influence of the surface unpolymerized layer in the cured surface of the adhesive material.

Examples 2 to 26 and Comparative Examples 2 to 10

Each example and comparative example was carried out in the same manner in Example 1, except that the combination of the adhesive material and the composite resin was changed to those shown in Table 5 and Table 6, and there were measured the adhesive strength of each dental filling/restoration kit and the sunlight stability of each composite resin. Table 5 and Table 6 show the results.

TABLE 5

| | | | Adhesive strength/MPa (standard deviation) | | | | |
|---|---|---|---|---|---|---|---|
| | | | Irradiation for 10 seconds | | Irradiation for 3 seconds | | |
| Example No. | Composite resin | Adhesive material | Enamel | Dentin | Enamel | Dentin | Sunlight stability |
| 1 | CR1 | B1 | 20.2 (2.1) | 19.0 (2.3) | 19.5 (2.0) | 18.3 (2.1) | ⊚ |
| 2 | CR2 | B1 | 19.1 (3.1) | 17.6 (2.8) | 16.9 (2.3) | 15.6 (2.1) | ⊚ |
| 3 | CR3 | B1 | 18.6 (2.5) | 17.2 (3.2) | 12.5 (2.4) | 11.0 (2.5) | ⊚ |
| 4 | CR4 | B1 | 19.7 (2.1) | 17.9 (3.8) | 14.3 (2.6) | 12.9 (2.7) | ⊚ |
| 5 | CR5 | B1 | 14.1 (3.3) | 13.2 (2.1) | 13.5 (2.4) | 12.9 (1.9) | ⊚ |
| 6 | CR6 | B1 | 19.8 (2.6) | 18.6 (3.3) | 18.9 (2.8) | 17.1 (1.8) | ⊚ |
| 7 | CR7 | B1 | 16.7 (2.9) | 15.1 (2.4) | 15.4 (3.1) | 14.8 (2.1) | ⊚ |
| 8 | CR9 | B1 | 18.2 (3.1) | 17.4 (4.6) | 17.5 (3.5) | 16.3 (2.5) | ⊚ |
| 9 | CR10 | B1 | 18.0 (4.2) | 16.8 (4.7) | 16.6 (3.2) | 16.2 (0.8) | ⊚ |
| 10 | CR11 | B1 | 17.0 (2.5) | 16.5 (2.4) | 16.1 (3.4) | 15.7 (2.0) | ⊚ |
| 11 | CR12 | B1 | 16.5 (2.1) | 16.2 (2.2) | 15.3 (2.0) | 14.6 (1.5) | ○ |
| 12 | CR13 | B1 | 17.5 (2.8) | 16.8 (2.1) | 16.6 (2.7) | 15.9 (1.4) | ⊚ |
| 13 | CR16 | B1 | 18.0 (3.7) | 17.1 (2.9) | 16.9 (3.3) | 16.5 (1.2) | ⊚ |
| 14 | CR17 | B1 | 17.2 (2.0) | 16.5 (2.1) | 16.0 (1.6) | 16.2 (1.3) | ⊚ |
| 15 | CR19 | B1 | 19.4 (3.6) | 18.3 (1.8) | 18.8 (2.0) | 17.0 (2.3) | ⊚ |
| 16 | CR20 | B1 | 20.7 (2.9) | 19.3 (2.2) | 19.7 (3.1) | 18.4 (1.9) | ⊚ |
| 17 | CR21 | B1 | 17.9 (1.8) | 17.0 (2.4) | 14.5 (2.5) | 12.9 (2.1) | Δ |
| 18 | CR22 | B1 | 18.8 (3.4) | 17.6 (1.9) | 14.6 (2.0) | 13.5 (2.3) | Δ |
| 19 | CR1 | B2 | 18.5 (3.0) | 21.7 (2.7) | 18.1 (2.9) | 21.0 (2.4) | Same as CR1 |
| 20 | CR1 | B3 | 19.5 (3.4) | 21.0 (3.8) | 19.0 (2.8) | 20.7 (1.6) | Same as CR1 |
| 21 | CR1 | B4 | 21.7 (2.5) | 20.5 (3.0) | 20.9 (2.3) | 20.1 (2.8) | Same as CR1 |
| 22 | CR1 | B5 | 18.3 (2.7) | 19.5 (3.1) | 17.9 (3.0) | 18.8 (2.5) | Same as CR1 |
| 23 | CR1 | B6 | 19.6 (3.4) | 18.9 (3.0) | 18.3 (2.5) | 17.0 (2.7) | Same as CR1 |
| 24 | CR1 | B7 | 12.2 (3.3) | 12.0 (2.1) | 9.6 (1.8) | 8.9 (1.2) | Same as CR1 |
| 25 | CR23 | B1 | 19.9 (2.4) | 19.4 (2.9) | 18.9 (2.5) | 18.0 (2.2) | ⊚ |
| 26 | CR24 | B1 | 20.6 (2.8) | 20.0 (3.1) | 16.1 (2.3) | 15.5 (1.8) | ⊚ |

TABLE 6

| | | | Adhesive strength/MPa (standard deviation) Free of polypropylene film | | | | |
|---|---|---|---|---|---|---|---|
| | | | Irradiation for 10 seconds | | Irradiation for 3 seconds | | |
| Comparative Example No. | Composite resin | Adhesive material | Enamel | Dentin | Enamel | Dentin | Sunlight stability |
| 1 | CR8 | B1 | 21.1 (3.2) | 20.7 (2.6) | 7.9 (2.1) | 3.1 (1.6) | ⊚ |
| 2 | CR8 | B2 | 19.5 (2.5) | 21.4 (1.7) | 5.4 (1.5) | 4.6 (2.2) | Same as CR8 |
| 3 | CR8 | B3 | 20.1 (2.9) | 21.3 (2.4) | 6.2 (2.9) | 4.2 (2.0) | Same as CR8 |

TABLE 6-continued

| | | | Adhesive strength/MPa (standard deviation) Free of polypropylene film | | | | |
| | | | Irradiation for 10 seconds | | Irradiation for 3 seconds | | Sunlight |
| Comparative Example No. | Composite resin | Adhesive material | Enamel | Dentin | Enamel | Dentin | stability |
|---|---|---|---|---|---|---|---|
| 4 | CR8 | B4 | 21.8 (2.1) | 21.6 (3.1) | 6.7 (2.7) | 5.1 (1.4) | Same as CR8 |
| 5 | CR8 | B5 | 19.3 (3.0) | 20.8 (3.9) | 5.0 (2.4) | 3.7 (0.9) | Same as CR8 |
| 6 | CR8 | B6 | 15.2 (2.4) | 14.6 (3.3) | 2.2 (1.0) | 1.8 (0.4) | Same as CR8 |
| 7 | CR14 | B1 | 15.8 (2.3) | 15.0 (2.0) | 2.5 (0.8) | 2.4 (1.1) | ⊚ |
| 8 | CR15 | B1 | 14.9 (4.4) | 14.1 (3.8) | 2.4 (0.9) | 1.5 (0.6) | ⊚ |
| 9 | CR18 | B1 | 14.9 (3.0) | 14.2 (2.7) | 2.1 (1.7) | 1.3 (0.8) | ⊚ |
| 10 | CR8 | B7 | 12.3 (2.7) | 12.0 (2.5) | 7.7 (2.2) | 7.2 (1.9) | Same as CR8 |

In Examples 2 to 26, visible light irradiation for both 10 seconds and 3 seconds provided high adhesive strength with respect to an enamel and a dentin. Note that, in Examples 16 and 17, in which a halomethyl group-substituted s-triazine derivative was used as a photoacid generator blended as a photopolymerization initiator in a composite resin, the adhesive strength was slightly lowered, compared with Examples 1 to 15, in which an aryliodonium salt was used as the photoacid generator. Further, the sunlight stability was good in all examples, but in Example 11, in which the composite resin was CR12 including an aliphatic amine compound at a relatively large content as a photopolymerization initiator, a change in color tone was remarkable, resulting in a lower evaluation.

On the other hand, in Comparative Examples 2 to 9, in which the composition of any one of the adhesive material and the composite resin that were used was, the adhesive strength was not sufficiently provided by at least visible light irradiation for 3 seconds.

Further, in Example 24, which was carried out in the same manner as in Example 1, except that there was used an adhesive material including, as a polymerizable monomer having an acidic group, MAC-10 containing a carboxylic acid group, which is a weak acidic group, instead of a polymerizable monomer containing a phosphate acidic group, the adhesive strength was slightly lowered, compared with Example 1. Further, when the results of Example 24 were compared with the results of Comparative Example 10, in which a composite resin free of a basic inorganic material was used, the ratio of improvement in adhesive strength of Example 24 to Comparative Example 10 was about a little under 25% in the case of visible light irradiation for 3 seconds to both an enamel and a dentin. Thus, the ratio of improvement was smaller than the ratio of improvement of Example 1 to Comparative Example 1, the ratio showing as many as several times of increase in the case of visible light irradiation for 3 seconds to both an enamel and a dentin.

Further, regarding Examples 1, 25, and 26, in which different kinds of fluoroaluminosilicate glass each having different specific surface areas were used as a basic inorganic material included in a composite resin, visible light irradiation for both 10 seconds and 3 seconds provided high adhesive strength with respect to an enamel and a dentin in Examples 1 and 25, but visible light irradiation for 3 seconds resulted in slight reduction in adhesive strength in Example 26, in which CR24 having a smaller specific surface area was used.

Example 27

4.0 g of PM, 4.0 g of Bis-GMA, 2.0 g of HEMA, 0.5 g of MF1, 1.5 g of water, and 14.0 g of AN were weighed, and the whole was mixed, yielding an adhesive material A solution. 0.7 g of PhB-TEOA, 0.17 g of HP, 27.0 g of AN, and 0.3 g of PMMA were weighed, and the whole was mixed, yielding an adhesive material B solution. The adhesive material A solution and the adhesive material B solution were used as a mixture, thereby serving as a chemical polymerization-type adhesive material B8.

The adhesive strength of the above-mentioned dental filling/restoration kit was measured by the adhesive strength measurement test carried out in Example 1, provided that the test was carried out in the form that the above-mentioned adhesive material A solution and the above-mentioned adhesive material B solution were mixed before the resultant mixture was applied in a pseudo cavity, and the resultant mixed adhesive material B8 was applied in the pseudo cavity and left to stand for 20 seconds, followed by drying by blowing compressed air for 10 seconds, but visible light was not irradiated afterward. The results were good, because visible light irradiation for 10 seconds exhibited an adhesive strength of 19.8 (2.8) MPa with respect to an enamel and an adhesive strength of 18.6 (2.0) MPa with respect to a dentin, and visible light irradiation for 3 seconds exhibited an adhesive strength of 19.1 (3.2) MPa with respect to an enamel and an adhesive strength of 17.8 (2.5) MPa with respect to a dentin.

Comparative Example 11

The adhesive strength measurement test carried out in Example 27 was carried out in the form that the composite resin CR8 free of a basic inorganic material was used. According to the results, visible light irradiation for 10 seconds exhibited an adhesive strength of 19.2 (2.3) MPa with respect to an enamel and an adhesive strength of 18.0 (2.8) MPa with respect to a dentin, and visible light irradiation for 3 seconds exhibited an adhesive strength of 6.5 (2.4) MPa with respect to an enamel and an adhesive strength of 2.3 (1.2) MPa with respect to a dentin. Thus, the adhesive strength was not sufficiently provided by at least visible light irradiation for 3 seconds, compared with Example 27.

What is claimed is:

1. A dental filling/restoration kit, comprising:
   a filling/restoring material (A) comprising:
   100 parts by mass of a polymerizable monomer having no acidic group (I);
   7 parts to 30 parts by mass of fluoroaluminosilicate glass having a 24-hour elution ion amount in a range of 15 to 50 meq/g of glass (II); and
   a photopolymerization initiator (III) formed by at least combining:
   an α-diketone compound (i);

an aliphatic amine compound (II);
an aromatic amine compound (iii); and
a photoacid generator (iv); and
an adhesive material (B), which is used for adhesion between a tooth and the filling/restoring material by curing the adhesive material before filling the filling/restoring material, the adhesive material comprising:
a polymerizable monomer including a polymerizable monomer having an acidic group (I); and
a polymerization initiator (II),
wherein the filing/restoring material is free of polymerizable monomers having an acidic group.

2. A dental filling/restoration kit according to claim 1, wherein the filling/restoring material (A) comprises tertiary amine compounds as the aliphatic amine compound (III) (ii) and the aromatic amine compound (A) (III) (iii).

3. A dental filling/restoration kit according to claim 1, wherein the adhesive material (B) further comprises water (III).

4. A dental filling/restoration kit according to claim 1, wherein the adhesive material (B) comprises a polymerizable monomer having a phosphate acidic group as an acidic group as the polymerizable monomer including a polymerizable monomer having an acidic group (I).

5. A dental filling/restoration kit according to claim 1, wherein the filling/restoring material (A) comprises a filler (IV).

6. A dental filling/restoration kit according to claim 1, wherein the dental filling restoration kit consists of the filling/restoring material (A) and the adhesive material (B).

\* \* \* \* \*